(12) United States Patent
Weibel et al.

(10) Patent No.: US 11,040,146 B2
(45) Date of Patent: Jun. 22, 2021

(54) DOSING APPARATUS FOR DISPENSING A FLUID UNDER ASEPTIC CONDITIONS

(71) Applicant: SHL Medical AG, Zug (CH)

(72) Inventors: Ludwig Daniel Weibel, Waldstatt (CH); Samuel Wyler, Abtwil (CH)

(73) Assignee: SHL MEDICAL AG, Zug (CH)

( * ) Notice: Subject to any disclaimer, the term of this patent is extended or adjusted under 35 U.S.C. 154(b) by 0 days.

(21) Appl. No.: 15/931,100

(22) Filed: May 13, 2020

(65) Prior Publication Data

US 2020/0297935 A1 Sep. 24, 2020

Related U.S. Application Data

(62) Division of application No. 15/006,285, filed on Jan. 26, 2016, now Pat. No. 10,653,846.

(30) Foreign Application Priority Data

Jan. 27, 2015 (EP) .................................... 15152703

(51) Int. Cl.
*A61M 5/315* (2006.01)
*A61M 5/145* (2006.01)
(Continued)

(52) U.S. Cl.
CPC ..... *A61M 5/31515* (2013.01); *A61B 5/14532* (2013.01); *A61J 1/2096* (2013.01);
(Continued)

(58) Field of Classification Search
CPC .............. A61M 5/1422; A61M 5/1454; A61M 5/1408; A61M 5/31515;
(Continued)

(56) References Cited

U.S. PATENT DOCUMENTS 1,516,032 A 11/1924 White
5,513,779 A 5/1996 Reich
(Continued)

FOREIGN PATENT DOCUMENTS

EP 0 701 061 A1 3/1996
EP 2 628 494 A1 8/2013
(Continued)

OTHER PUBLICATIONS

OOE Work Product Corresponding to EP 15 152 703.3 mailed Nov. 6, 2017.
(Continued)

*Primary Examiner* — Theodore J Stigell
*Assistant Examiner* — James D Ponton
(74) *Attorney, Agent, or Firm* — McDonnell Boehnen Hulbert & Berghoff LLP

(57) ABSTRACT

The dosing apparatus comprises a conveying device (5), which is driven by at least one conveying drive (4), for conveying fluid from the interior (3) of a container (2). The fluid by means of the conveying device (5) is conveyable from the container to a dispensing opening (6). The conveying device (5) comprises a cylinder (7) having at least one intake opening (11) and at least one outlet opening (12) on an inner cylinder wall (8), and a first piston (9) and a second piston (10). The first piston (9) and the second piston (10) are mounted within the cylinder (7) so as to be displaceable in the longitudinal direction. Furthermore, the first piston (9) and the second piston (10) between the end sides thereof and together with a portion of the inner cylinder wall (8) delimit a variable fluid volume (17).

11 Claims, 25 Drawing Sheets

Figure 1:
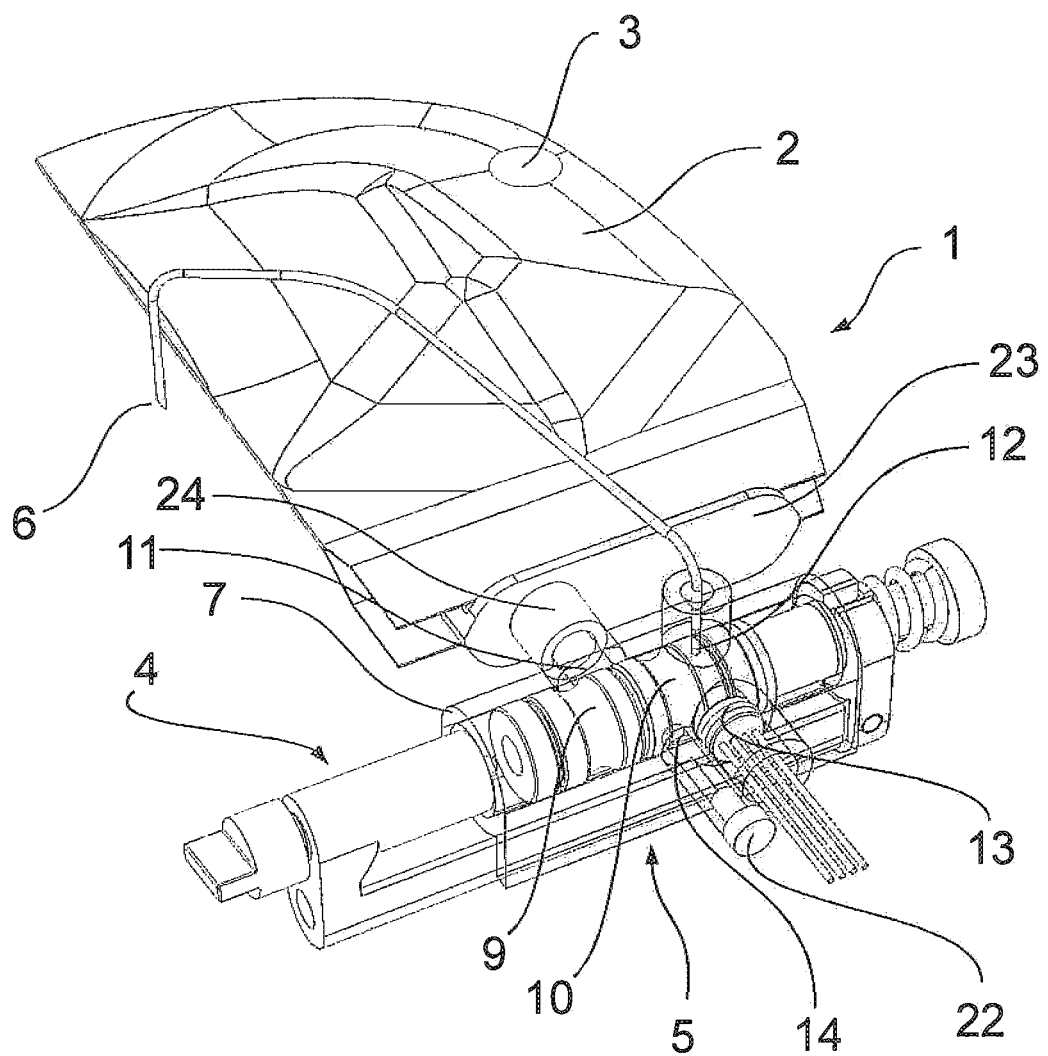

(51) Int. Cl.
*F04B 7/04* (2006.01)
*F04B 9/02* (2006.01)
*A61M 5/14* (2006.01)
*A61B 5/145* (2006.01)
*A61J 1/20* (2006.01)
*A61M 5/142* (2006.01)
*F04B 13/00* (2006.01)

(52) U.S. Cl.
CPC ........ *A61M 5/1422* (2013.01); *A61M 5/1454* (2013.01); *F04B 7/045* (2013.01); *F04B 9/02* (2013.01); *F04B 13/00* (2013.01); *A61M 5/1408* (2013.01); *A61M 5/1413* (2013.01); *A61M 2005/14533* (2013.01); *A61M 2205/3331* (2013.01)

(58) Field of Classification Search
CPC ......... A61M 2005/14533; A61M 2005/14268; A61B 5/14532; A61J 1/2096; F04B 7/045; F04B 7/02; F04B 13/00
See application file for complete search history.

(56) References Cited

U.S. PATENT DOCUMENTS

| | | | |
|---|---|---|---|
| 2001/0025189 A1* | 9/2001 | Haueter | H05K 7/10 607/62 |
| 2002/0169439 A1* | 11/2002 | Flaherty | A61P 3/10 604/891.1 |
| 2003/0233069 A1 | 12/2003 | Gillespie, Jr. et al. | |
| 2005/0177111 A1 | 8/2005 | Ozeri et al. | |
| 2006/0270961 A1* | 11/2006 | Costa | A61M 1/3683 604/6.15 |
| 2010/0121306 A1* | 5/2010 | Yodfat | A61M 5/14244 604/500 |
| 2011/0073620 A1 | 3/2011 | Verrille | |
| 2011/0178461 A1 | 7/2011 | Chong et al. | |
| 2011/0196337 A1 | 8/2011 | Brandt et al. | |
| 2014/0276537 A1 | 9/2014 | Kruse | |
| 2015/0119804 A1 | 4/2015 | Seeley et al. | |
| 2015/0290389 A1* | 10/2015 | Nessel | F04B 3/00 604/500 |
| 2018/0126097 A1 | 5/2018 | Kamen et al. | |
| 2018/0126098 A1 | 5/2018 | Sharma et al. | |

FOREIGN PATENT DOCUMENTS

| | | |
|---|---|---|
| GB | 1 508 665 | 4/1978 |
| WO | 2014/090745 A1 | 6/2014 |
| WO | 2014/207532 A1 | 12/2014 |

OTHER PUBLICATIONS

European Search Report Corresponding to 15152703 dated Aug. 19, 2015.

\* cited by examiner

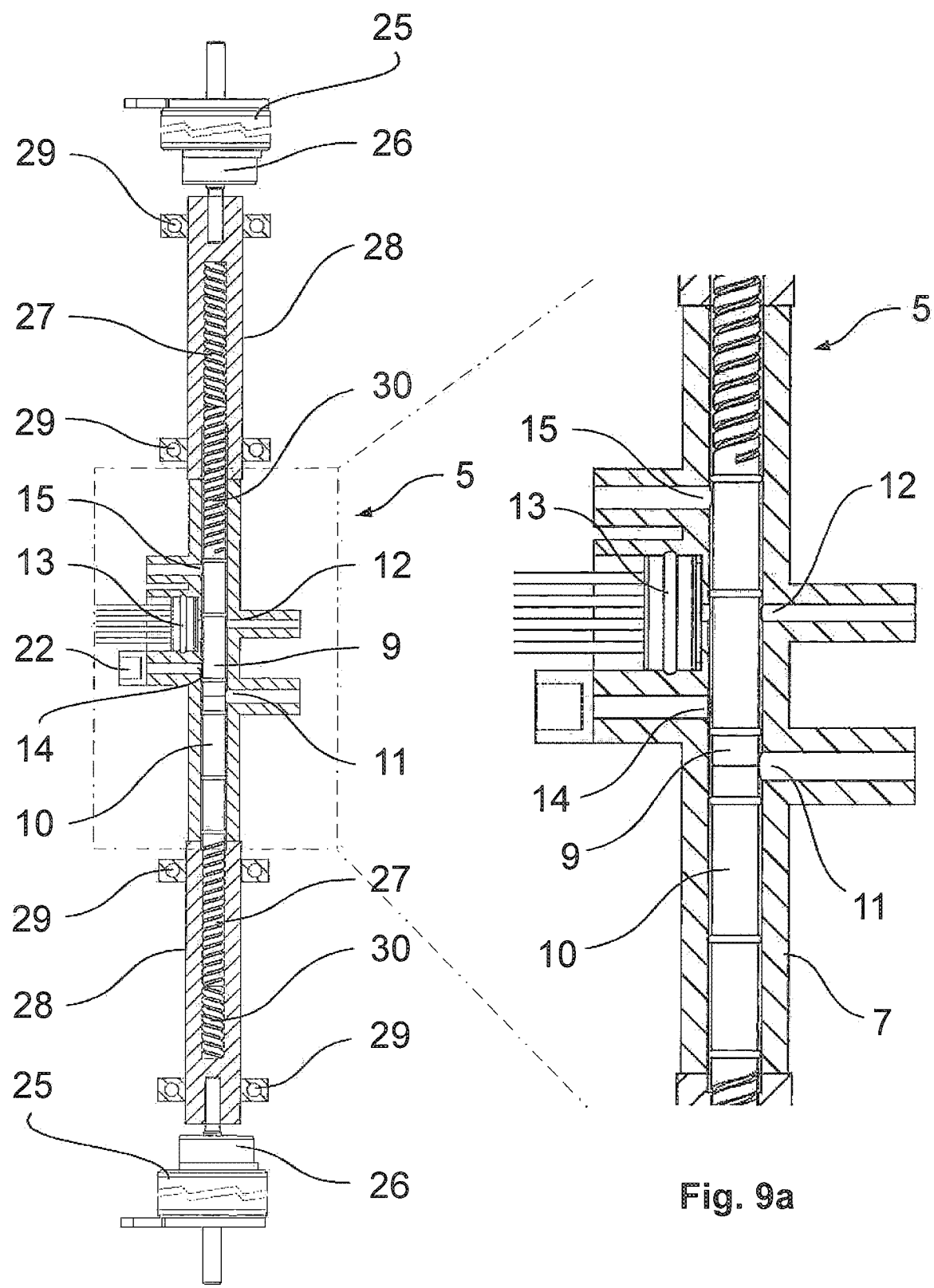

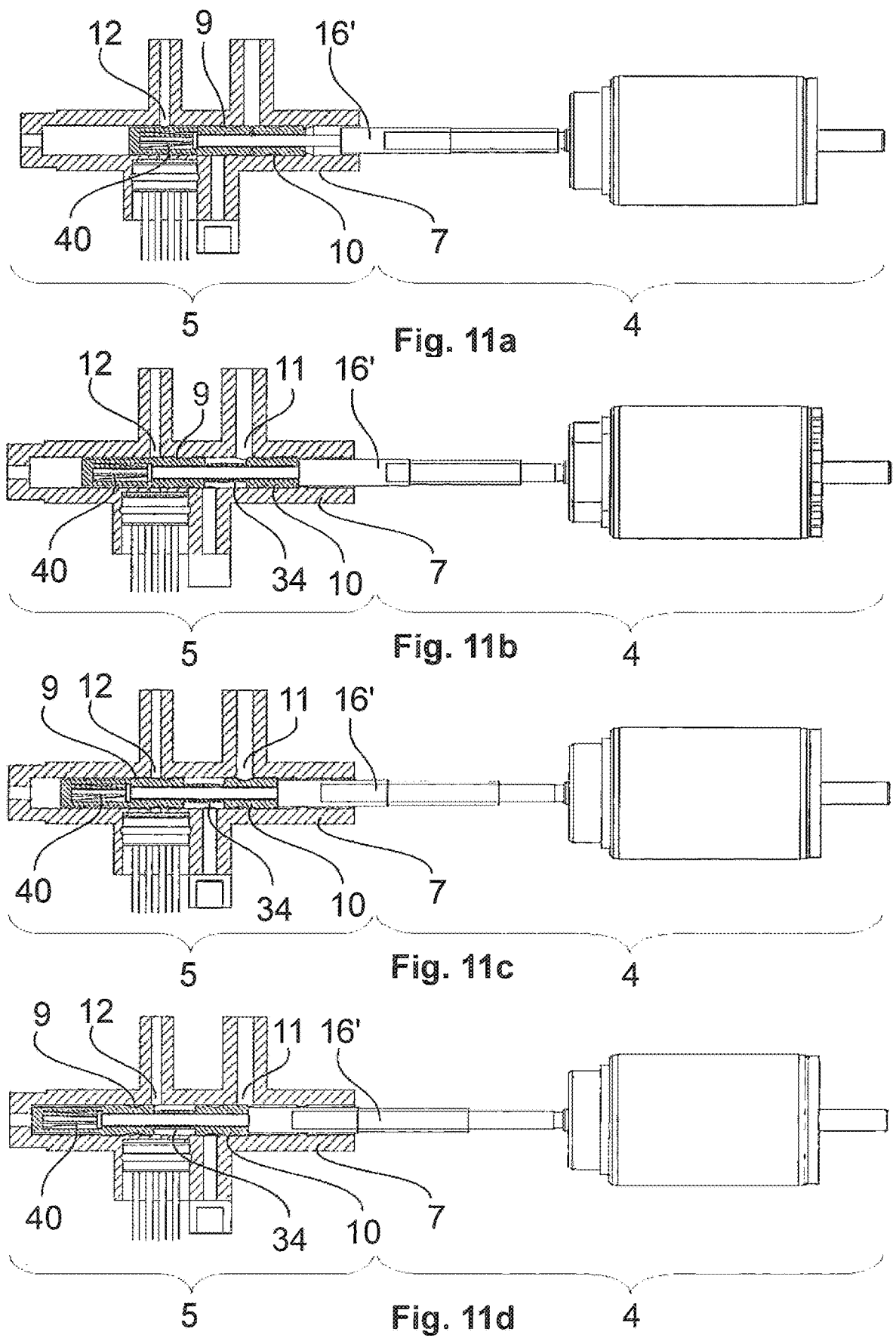

DOSING APPARATUS FOR DISPENSING A FLUID UNDER ASEPTIC CONDITIONS

The invention relates to a dosing apparatus for dispensing a fluid under aseptic conditions, according to the preamble of claim 1.

When administering fluid formulae of active pharmaceutical ingredients to a patient it is in most cases necessary to dispense well defined volumes. Often the medication here has to be injected into the patient's body. To this end, injection syringes, medication pens, or medication pumps are employed for parenteral injection.

In this context, injection syringes which are intended for single use are widely used, due to the low price and ready availability of said injection syringes. However, the use of such syringes requires trained personnel for the flawless dispensation thereof. In this way, the liquid formula has to be optionally drawn from a respective vial, wherein attention has to be paid inter alia to a sufficient absence of bubbles and to sterile conditions. This is problematic in particular in the case of preparations which have to be dispensed over a prolonged period of time. In this way, patients suffering from diabetes often have to self-administer a dosage of insulin a number of times per day under widely variable conditions, for example.

Injection syringes in such cases are therefore often replaced by so-called medication pens. These offer the advantage of being able to successively dispense a plurality of dosages of a preparation. To this end, said medication pens dispose of a replacable storage container (for example a vial) which is supplied so as to be pre-filled and sterile and is insertable into the medication pen. However, the application in the case of a medication pen must also be performed by the actual patient. This requires a number of skills in terms of correct usage and dosing. Furthermore, attention has to be paid at all times to cleanliness and hygiene.

In contrast, medication pumps are suited to being attached to a patient's body over a prolonged period of time and to dispense a preparation in a continuous manner or according to an individually predefined schedule, respectively. Medication pumps of this type typically comprise a container for the liquid formula, and a conveying device (for example a pump) which conveys the medication to a connector of the device or to an injection system. The injection system in certain cases may comprise an indwelling cannula which remains in the patient's body during the entire dispensing period.

In this way, US 2005/0177111 A1, for example, shows a micro-infusion pump for dispensing medication to a patient in a controlled manner. Said pump is configured substantially as a syringe pump and disposes of an integrated drive mechanism. Dispensing of the liquid formula from the pump to the patient is performed via a flexible infusion tube. The pump which may be used for dispensing insulin to a diabetic, for example, is sufficiently compact so as to be attached to patient's body. Moreover, the device disposes of a switching circuit for controlling the pump actuation, and a pressure sensor for measuring the pressure exerted on the syringe piston, and a further sensor for determining the position of the syringe piston.

Medication pumps of this type have the advantage of being able to dispense a preparation to a patient continuously without any active participation of the latter. In this way, said medication pumps differ fundamentally from injection syringes and from medication pens by having manually performed single discharges. However, the desired reliability of the pump is often not adequately ensured with sufficient safety, or the accuracy of the dispensed quantity of medication does not meet the regulatory requirements. Moreover, only a single liquid formula may typically be dispensed in a plurality of dosages by medication pumps. Furthermore, dispensing a preparation by a medication pump is typically performed according to an established schedule, without consideration for the patient's current state. In this way, it would be desirable in the case of a patient with diabetes, for example, to perform the dispensing of insulin under constant monitoring of the blood-sugar level and to continuously adapt dispensing to the latter.

On account of the life-preserving function of dispensing specific medications, there are moreover more stringent requirements set for the operational reliability of a medication pump. Since devices of this type are worn on a patient's body over a prolonged period, there is furthermore need for a medication pump to be designed to be as rugged and compact as possible. Moreover, on account of the required sterility, at least partial embodiment as a disposable unit is desirable. Accordingly, there is need for a construction which is as simple and as cost-effective as possible to be provided.

However, the issue in terms of exact dosing is not only encountered in the case of aseptic dispensing of fluid pharmaceuticals to patients, but also when filling vials, pouches, or syringes in pharmaceutical production. In the filling stations employed there, to this end peristaltic pumps are used, for example. While pumps of this type, due to the active principle thereof, guarantee a high degree of sterility, their use does entail a number of disadvantages. For constructive reasons, in this way the service life of the tube in the case of a peristaltic pump is limited. Moreover, abrasion of the tube may contaminate the conveyed goods, representing a potential risk to the patient. Last but not least, the dosing accuracy which is achievable in pumps of this type is subject to certain limitations.

It is thus an object of the invention to overcome the disadvantages of the prior art. In particular, it is an object to provide a dosing apparatus for dispensing a fluid under aseptic conditions, which is employable in a versatile manner and which is reliable and rugged and comfortable in terms of handling. The apparatus is to be employable both in a mobile as well as stationary manner. Moreover, the dosing apparatus is to guarantee patient safety which is as high as possible, is to have a simple and compact construction, and is to be manufacturable in a cost-effective manner.

These objects are achieved by a dosing apparatus which has the features in claim 1.

Said dosing apparatus comprises a conveying device, which is driven by at least one conveying drive, for conveying fluid from the interior of a container. The fluid here by means of the conveying device is conveyable from the container to a dispensing opening. The invention is distinguished in that the conveying device comprises a cylinder having at least one intake opening and at least one outlet opening on an inner cylinder wall, and a first piston and a second piston. The first piston and the second piston here are mounted within the cylinder so as to be displaceable in the longitudinal direction. Furthermore, the first piston and the second piston between the end sides thereof and together with a portion of the inner cylinder wall delimit a variable fluid volume.

A dosing apparatus of this type having two pistons in one cylinder allows a variety of possibilities. Moreover, the dosing apparatus may be embodied so as to be without valves, on account of which a particularly simple construction principle is achieved. This not only allows for a dosing apparatus according to the invention to be manufactured in a particularly cost-effective manner, but also enhances the reliability thereof during prolonged operation. Moreover, a construction without valves enables a very high degree of miniaturization, such as is required in portable insulin dispensing systems, for example.

The intake opening and the outlet opening may be disposed on the cylinder so as to be offset in the longitudinal direction. This enables the employment of pistons in which the longitudinal axis of the cylinder runs perpendicularly to the end side. On account thereof, the construction of the conveying device is further simplified.

The intake opening may be fluidically connectable with the interior of a container, and the outlet opening may be fluidically connectable with the dispensing opening. On account thereof, the fluid may be conveyed by the conveying device from the interior of a container directly to the dispensing opening.

The dosing apparatus may have a pressure sensor which is preferably disposed on the cylinder, in particular in the longitudinal direction so as to be level with the outlet opening, and which directly measures the fluid pressure. On account of the presence of a pressure sensor of this type, the dispensing process of the fluid may be monitored in real time and actual dispensing of a medicine to a patient may be ensured. Furthermore, not only may excess pressure in the fluid-conducting systems be avoided, but also unintentional leaking of fluids as well as potential injuries to a patient, caused by excess pressure.

The dosing apparatus may additionally comprise a container, which in particular is partially collapsible, having an interior. In this embodiment, the dosing apparatus forms a compact dispensing unit by way of which fluid may be dispensed to a patient over a prolonged period, for example.

An at least partially collapsible design embodiment of the container has the advantage that there is no need for venting openings to be present, in order to equalize by way of air subsequently streaming into the container any negative pressure which is created on account of the removal of the fluid. Moreover, collapsible containers, such as pouches, may be configured so as to be flat, resulting in a space-saving arrangement in particular in the case of portable dosing apparatuses. However, the container may also be embodied so as to be rigid, having a trailing piston which may optionally be biased by a compression spring.

A dosing apparatus of this type may additionally comprise a filling opening which by displacing the first piston and the second piston within the cylinder is fluidically connectable with the intake opening. This enables filling of the container through the conveying device, making further filling infeed lines superfluous. In this way, the empty container may be inserted into the dosing apparatus and only be filled by a user prior to the application of the dosing apparatus, for example.

Here, the filling opening and the intake opening may be disposed on the cylinder so as to be offset in the longitudinal direction. In this configuration, the conveying device in relation to the fluid path required for filling may also fulfil the function of a valve.

In order for an optimal filling process to be provided, the filling opening may be fluidically connectable with a coupling means, in particular a Luer coupling, for coupling to a fluid source. Advantageously, a valve device, preferably a duckbill valve, which blocks the filling opening towards the outside in relation to a fluid stream from the conveying device, is disposed in fluid communication between the filling opening and the coupling means. A dosing apparatus which is embodied in this manner may be coupled to well-established containers having liquid pharmaceutical formulae. However, the filling opening may also have a septum which is penetrable by a filling cannula and which closes again in a fluid-tight manner once the cannula has been removed.

It is understood that pre-filled containers which in the supplied state are already filled with the fluid and are coupled to the dosing apparatus or can be coupled thereto, respectively, may also be employed.

The conveying device may comprise at least two intake openings which are disposed on the cylinder so as to be offset in the longitudinal direction. On account of the presence of a plurality of intake openings, various fluids may be selectively dispensed by way of one and the same dosing apparatus. This may optionally be performed separately or by mixing the two fluids by way of the fluid conveying device.

In this way, each intake opening may be fluidically connectable with the interior of a separate container which is assigned to said interior and is in particular partially collapsible, for example. It is conceivable, for example, that liquid formulae of the same active ingredient in dissimilar concentrations are located in the two containers. On account thereof, it is possible for a patient to be infed a medicine in a very wide dosing range. However, it is also conceivable that two dissimilar liquid formulae with dissimilar active ingredients are present in the two containers. This allows that one or the other active ingredient is dispensed to a patient, depending on the situation. A further application example of a dosing apparatus of this type is the continuous dispensing of a saline solution from a first container to a patient, so as to keep open a previously applied catheter access. In the case of such an application, an active-ingredient solution may be dispensed via the catheter to the patient from a second container, when and if required.

However, at least two intake openings may in each case be fluidically connectable to a discrete and separate interior of a container, wherein the discrete and separate interiors are designed in such a manner that at least two fluids are receivable in the container, so as to be separate from one another. Such a multi-chamber container enables a dosing apparatus according to the invention, which offers the above-described application possibilities but has a more compact and more favourable construction principle, to be provided.

Both a multi-chamber container as well as a plurality of single-chamber containers may be advantageous or, depending on the case, even be required in the case of active pharmaceutical ingredients which in the form of a solution cannot be stored over a prolonged period. Active ingredients of this type are often marketed in solid form, for example as a lyophilisate. A dosing apparatus according to the invention having two or more container chambers allows the active ingredient to be provided in a first chamber and the solvent in a second chamber. Preferably, the conveying device here is disposed in fluid communication between the chamber with the active ingredient, the chamber with the solvent, and the dispensing opening in such a manner that the solvent is conveyable into the chamber with the active ingredient. In this way, dissolution of the active ingredient immediately prior to dispensing of the formula to a patient may be achieved. The same conveying device is thereafter employable for conveying the solution of the active ingredient, which is ready for dispensing, to the dispensing opening.

"Disposed in fluid communication" here refers to an arrangement in the sense of a fluidically communicating interaction between components. An arrangement of one element being "disposed in fluid communication" between two components thus has at least one fluid path which via the element leads from one component to the other.

At least one container may additionally comprise a closure piece, wherein the closure piece in particular is fixedly disposed in the container and via a connection duct is fluidically connectable to the conveying device. Such a closure piece prevents the container collapsing when fluid is suctioned by the conveying device. The closure piece may furthermore be utilized for integrating parts of the conveying device in a container. Here, no or only a few fluid-tight connections which may be prone to leaking need to be created. In the case of a suitable configuration, the dosing apparatus may only require one fluid-tight connection which, for example, connects the outlet opening of the conveying device with the dispensing opening of the dosing apparatus.

The closure piece may be configured as an integral injection-moulded part, for example, in which parts of the conveying device and/or of fluid ducts and fluid openings which adjoin the former may be configured so as to be fixedly interconnected. In this way, fluid-conduction components may be integrated in the container, this enabling the installation size of the dosing apparatus to be reduced and/or the reliability thereof to be enhanced, for example.

The closure piece may furthermore have a filling opening which is open toward the outside in a closable manner and communicates with the interior of the container. In order for the dosing apparatus to be filled under the exclusion of air, the entire fluid-conducting system may be evacuated through such a filling opening.

The conveying device may additionally comprise an analysis opening which is disposed on the cylinder so as to be offset in the longitudinal direction in relation to the intake opening or to the intake openings and to the outlet opening, and is fluidically connectable with an analysis device. Apart from actually dispensing fluid in a dosed manner per se to a patient, this also enables liquids to be received for an analysis thereof. The fluid to be analyzed here is pumped through the analysis opening in or through an analysis device. The analysis device here may be a conventional glucose measuring strip or a spectrometer, for example. It is conceivable in this way that a specimen is taken from the own body fluid of a patient suffering from diabetes and analyzed, so as to determine the dosage of an insulin formula. On account thereof it is possible for the patient's blood-sugar level to be regulated in a fully automatic manner.

The first piston may be drivable by a first conveying drive, and the second piston may be drivable by a second conveying drive. This enables the two pistons to be driven in a mutually independent manner, on account of which a dosing apparatus of this type is suitable for a multiplicity of applications.

However, the first piston and the second piston may also be drivable by a common conveying drive. The flexibility of such a configuration is indeed lower than that of said configuration described above, but a dosing apparatus of this type may be implemented in a more favourable manner. In this way, at least one piston may be operatively connectable with the conveying drive in an indirect manner. On account thereof, it is possible for the two pistons to be drivable by a common drive and to nevertheless perform dissimilar stroke movements, on account of which the volume which is delimited by the two end sides of the pistons and of the inner cylinder wall is variable across an operating cycle of the conveying device, which is mandatory for a pumping effect.

In this context, a piston which is operatively connected to a conveying drive in a direct manner refers to a piston which always performs a stroke movement when the conveying drive moves. As opposed thereto, a piston which is operatively connected to a conveying drive in an "indirect" manner refers to a piston which only under specific circumstances performs a stroke movement when the conveying drive moves.

One potential embodiment of such a dosing apparatus lies in that a piston which is operatively connectable to the conveying drive in an indirect manner is operatively connectable to the conveying drive via a spring element which is preferably disposed in the interior of said piston. Moreover, the first piston and the second piston may be configured so as to be integral and be interconnected via a bellows. This design embodiment enables the conveying device to be implemented in a particularly simple construction principle. This construction form of the conveying device is also suitable as a general design principle for piston pumps.

At least one conveying drive may be configured as a spindle drive. A spindle drive has the advantage that a comparatively high force is exertable on the piston, using a well-established electric motor which generates a comparatively minor torque, on the one hand. Moreover, the piston position may be precisely set by way of a suitable motor controller, for example by way of a step-motor controller.

However, at least one conveying drive may also comprise a cam gear. An embodiment of this type has the advantage that almost any arbitrary piston movement is achievable by way of a suitable geometry of the cam disc. Furthermore, a cam gear is implementable in a very cost-effective manner, and in comparison with a spindle drive, allows significantly faster piston movement.

It is understood that the conveying drive or the conveying drives or the pistons per se, respectively, may be monitored by a monitoring device which is disposed in the dosing apparatus. In this way it may be ensured that a current piston position corresponds to an expected position.

The conveying drive or the conveying drives may be conceived so as to be coupleable to the conveying device, such that a drive unit may be configured so as to be separable from a dispensing unit of the dosing apparatus. This may be advantageous in the case of portable insulin dispensing systems, for example, in which the drive unit as a reusable module may be decouplable on dispensing units which are in each case unused. The drive unit preferably comprises an energy accumulator for the conveying drive and a controller unit for controlling the dosing apparatus. Likewise, an analysis device and/or communication means may be provided in the drive unit.

A dosing apparatus according to the invention may comprise an injection device for preferably continuously and subcutaneously dispensing fluid to a patient. On account thereof, it is possible for a dosing apparatus according to the invention to be attached to the body surface in the case of a diabetic, for example, so as to dispense a medicinal fluid, for example an insulin solution, to the patient over a prolonged period.

The dosing apparatus may comprise a drive module and a dispensing module, which are configured so as to be connectable and separable from one another by a user. The drive module here may comprise at least parts of the conveying drive, in particular and optionally a rotary drive and/or optionally an application drive of an injection device. The dispensing module may have at least the container as well as the conveying device, and optionally the injection device.

One further embodiment of a dosing apparatus according to the invention is suitable for use with a filling station filling for fluid under aseptic conditions. In such a dosing apparatus the first piston and the second piston are connected to in each case one piston rod. Here, at least one piston rod is curved in such a manner that a portion runs in the opposite direction, so as to be parallel with the piston thereof. Furthermore, the conveying device may comprise a housing which is connected to the cylinder, preferably in an integral manner, and has a free space for the curved region of a piston rod, and a parallel guide for that region which runs in the opposite direction, so as to be parallel with the piston thereof. The housing may have a catchment volume for catching fluid. Such a catchment volume in the case of an intended operation in a vertical orientation of the conveying device may catch fluid which streams past the piston, and may be emptied at regular temporal intervals by way of an outlet opening. The outlet opening may accordingly be configured so as to be closable.

With a view to the manufacturing tolerances required and to the targeted service life, a conveying device of this type is advantageously made from metal, in particular from stainless steel. The metallic parts may additionally have non-metallic coating. It goes without saying that such a dosing apparatus may also be equipped with sensors, such as pressure sensors or temperature sensors.

A dosing apparatus of this type, on account of the simple construction type without valves and without seals or piston rings, is particularly well suited to be employed in a filling station in pharmaceutical production, as said dosing apparatus is easy to disassemble, clean, and sterilize. However, so-called cleaning in place (CIP) is also conceivable, wherein back-flushing of the piston is performable using additional connectors on the cylinder.

Figure 3:
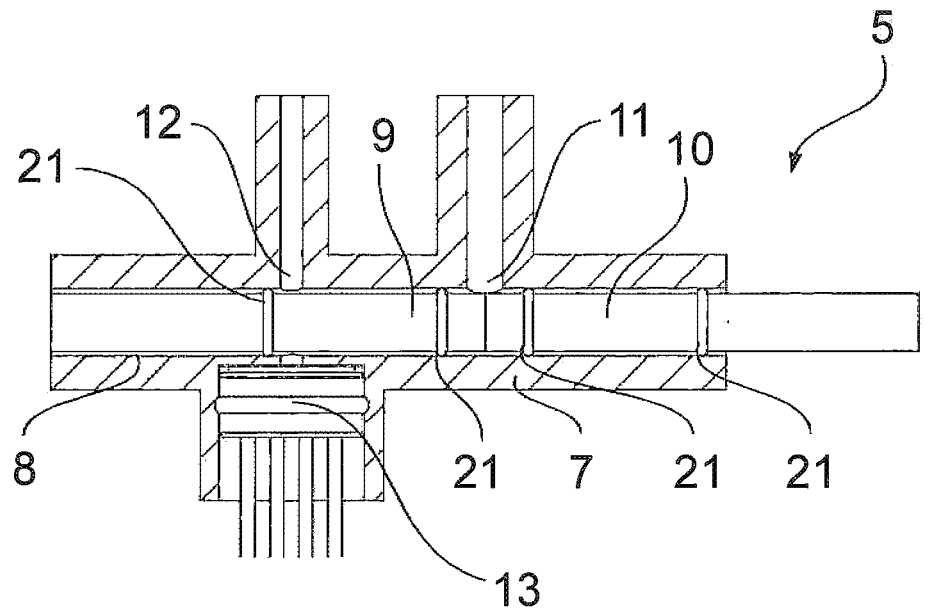
Figure 6:
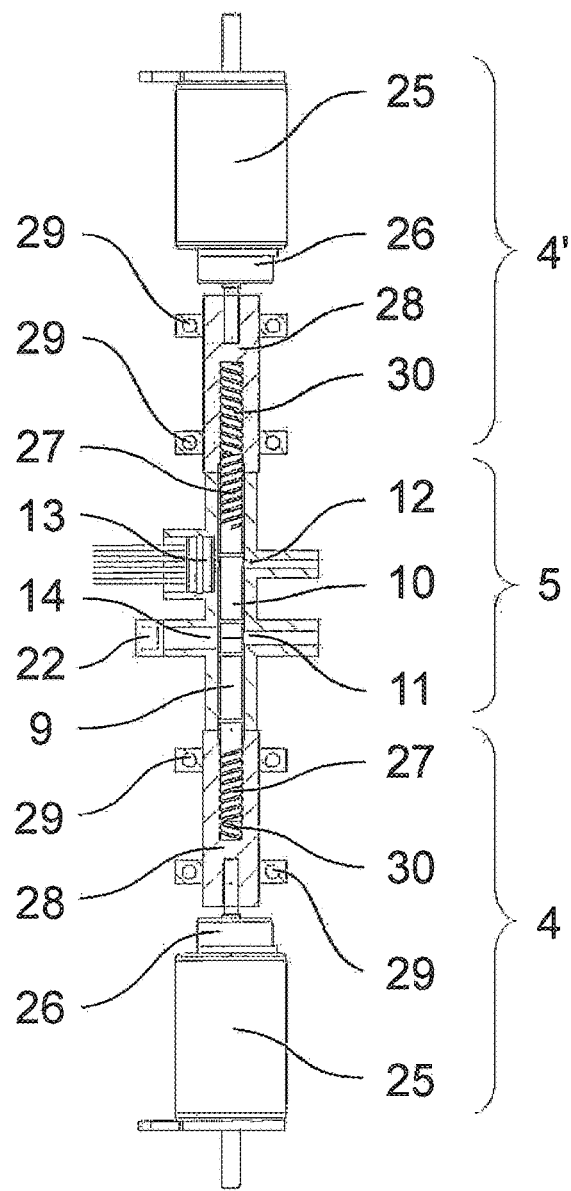
Figure 7:
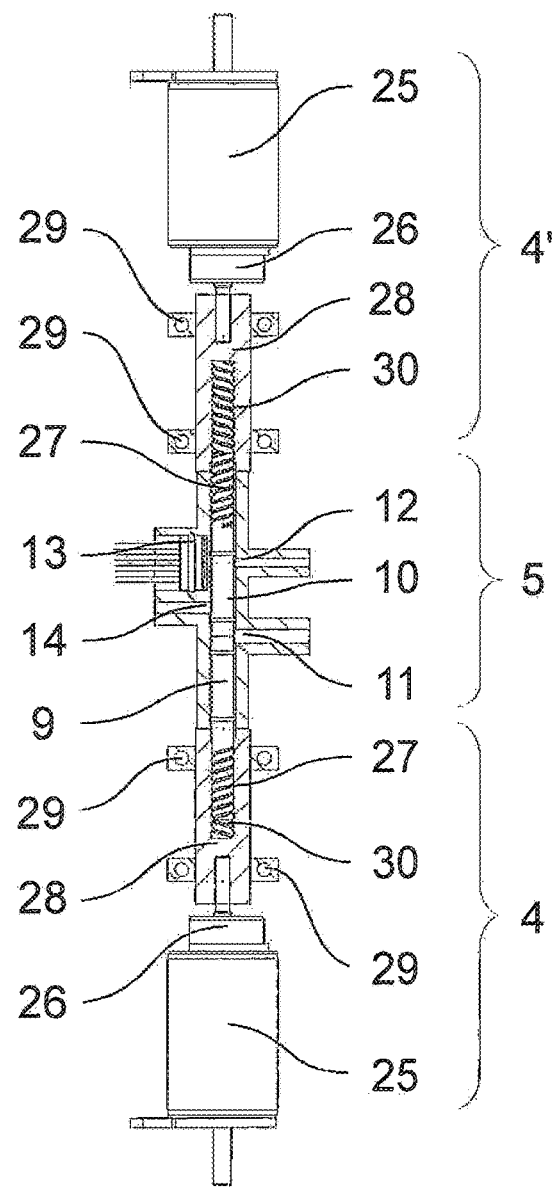
Figures 8, 8A:
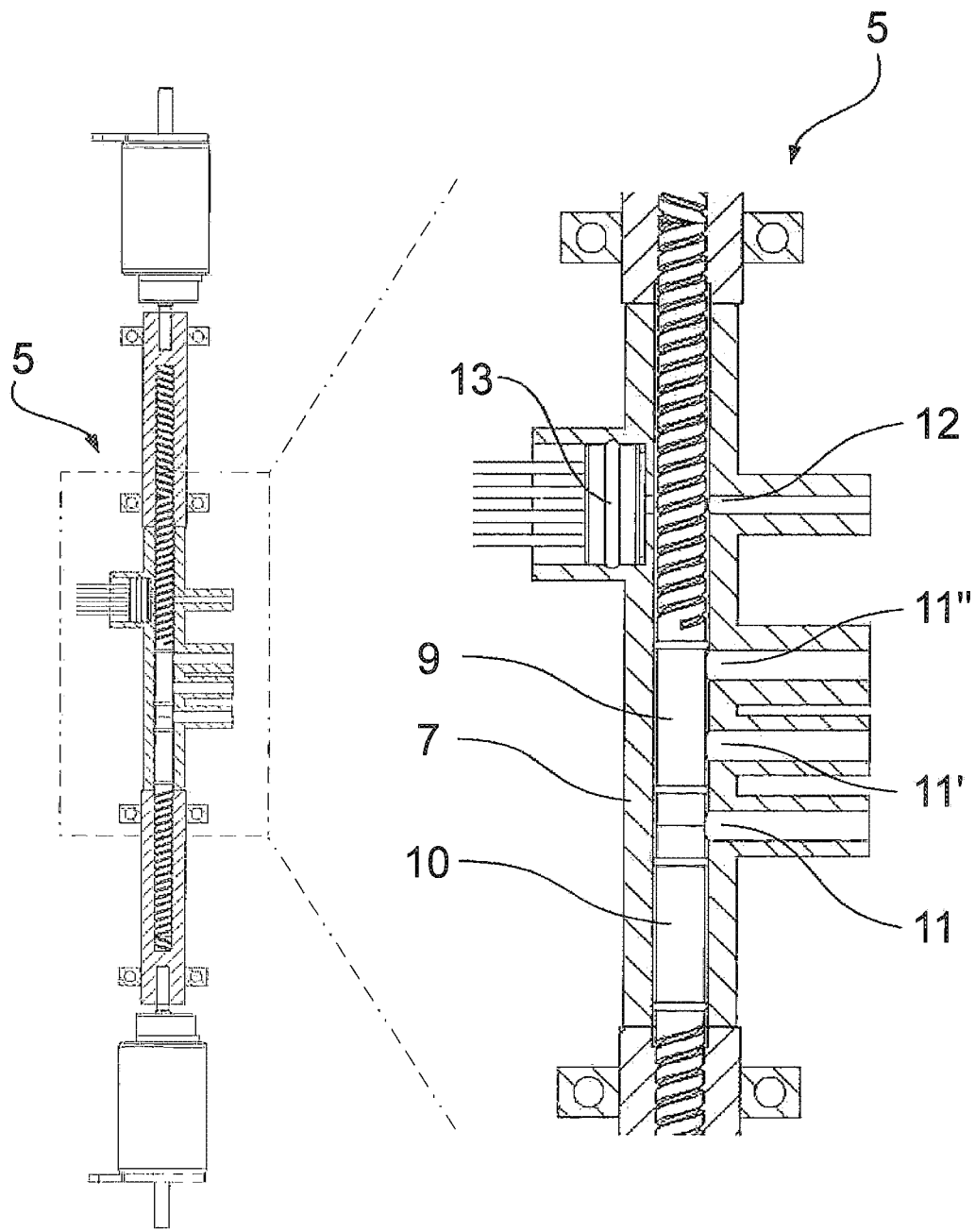
Figure 12A:
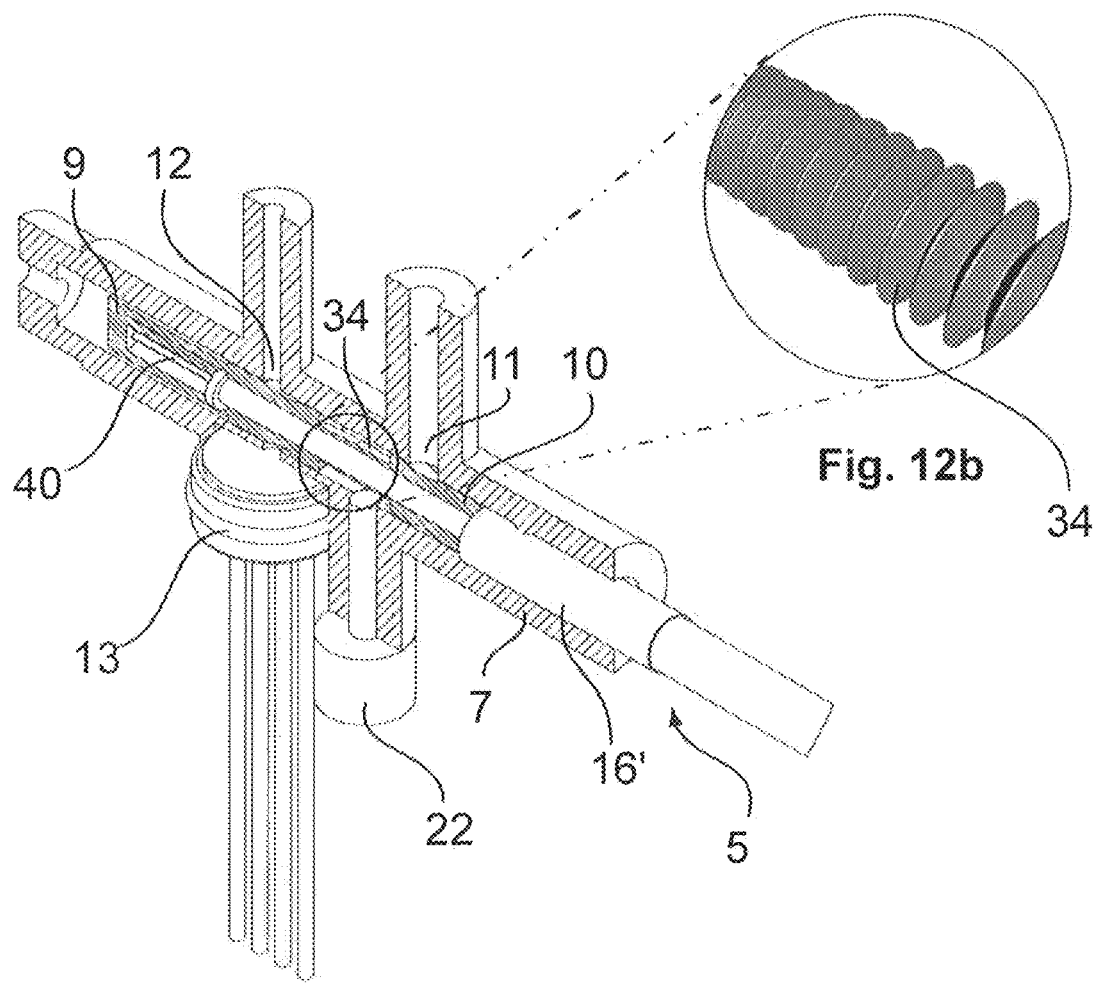
Figure 13A:
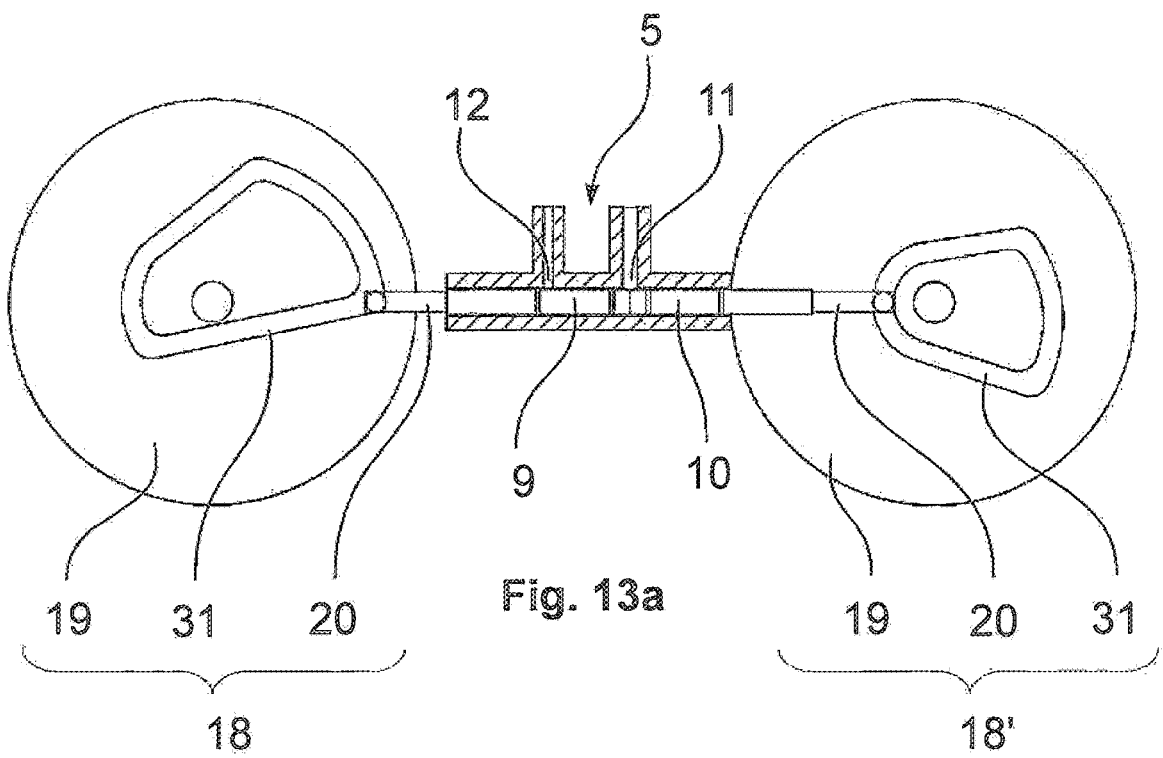
Figure 13B:
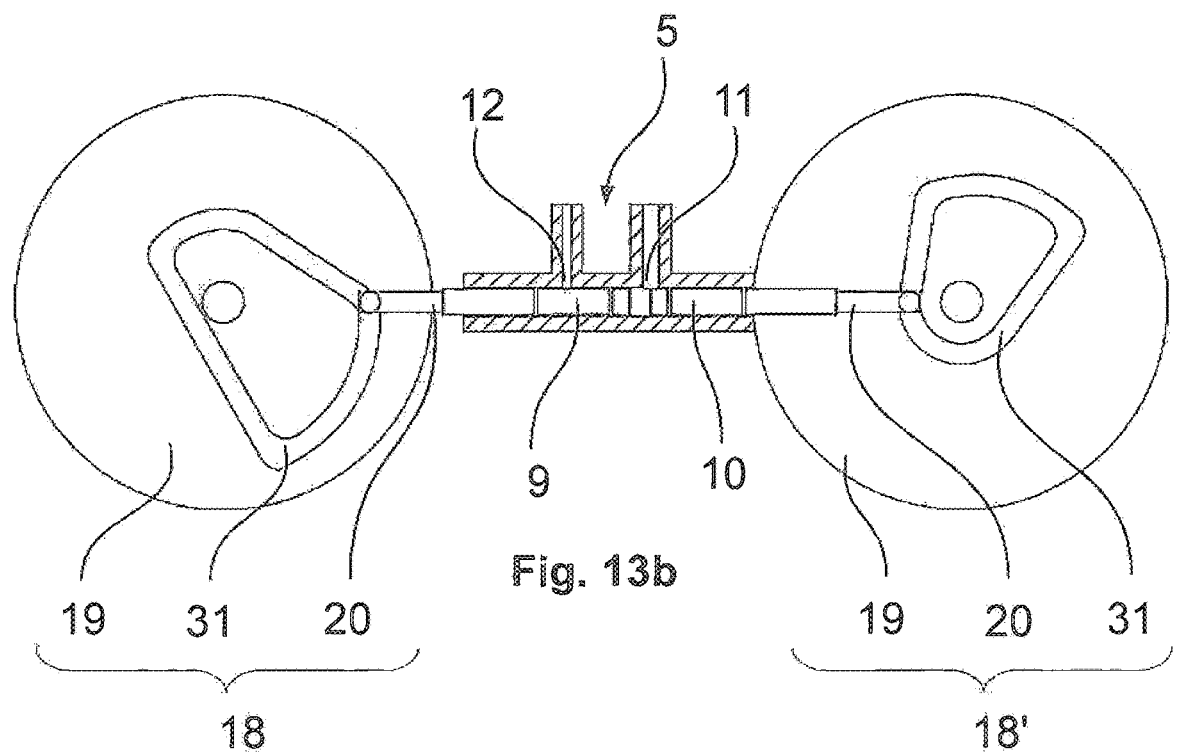
Figure 13C:
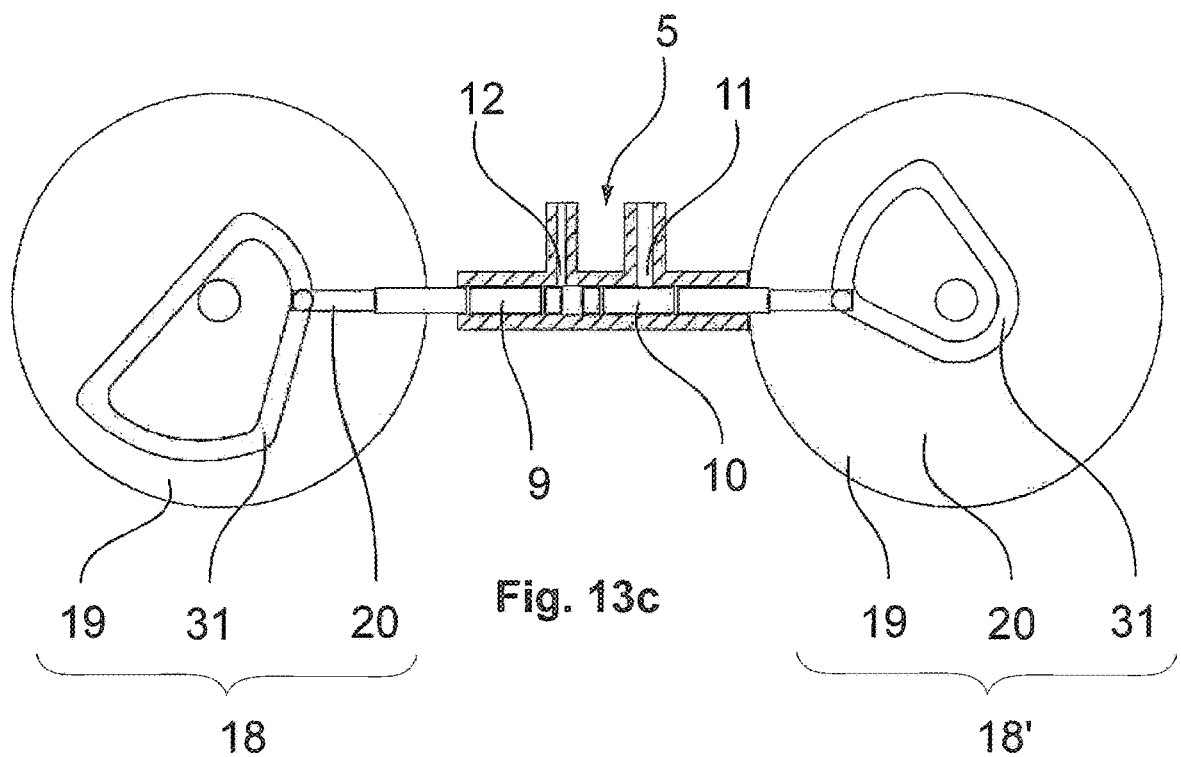
Figure 13D:
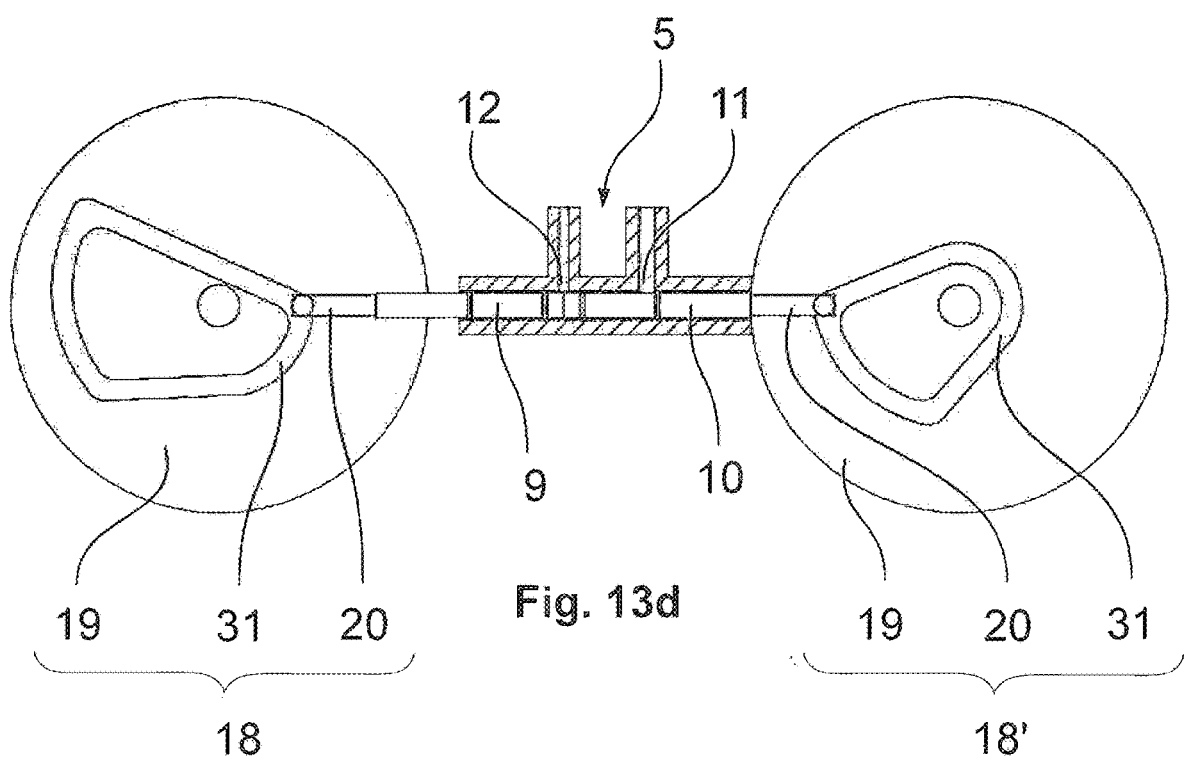
Figure 14A:
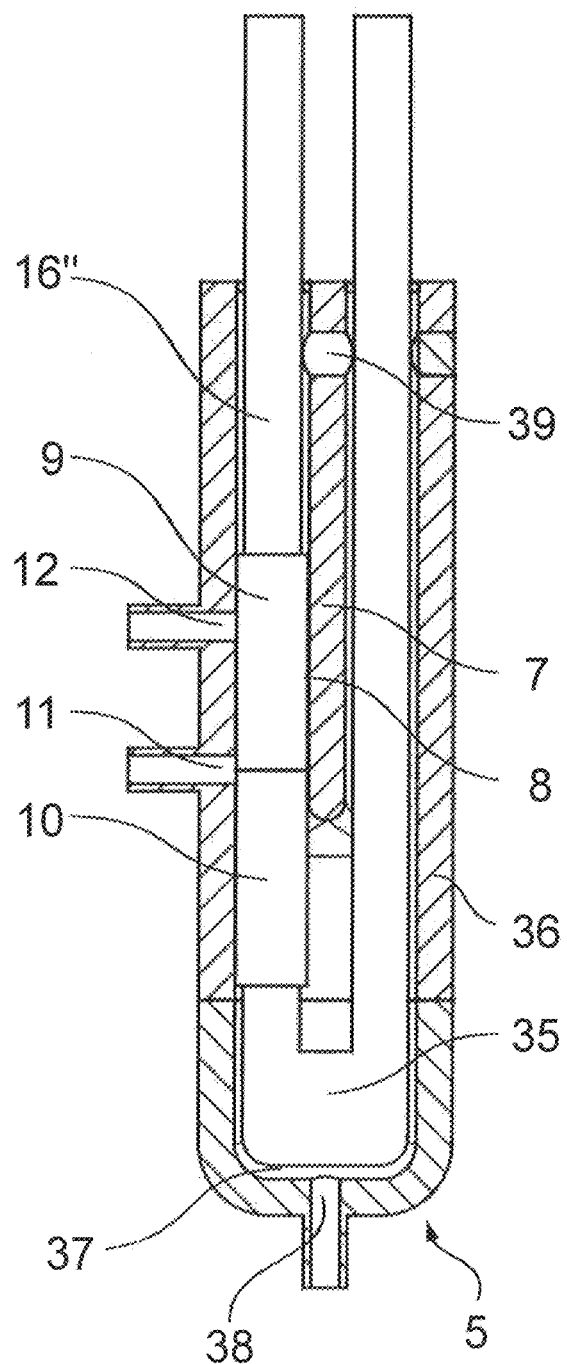
Figure 14B:
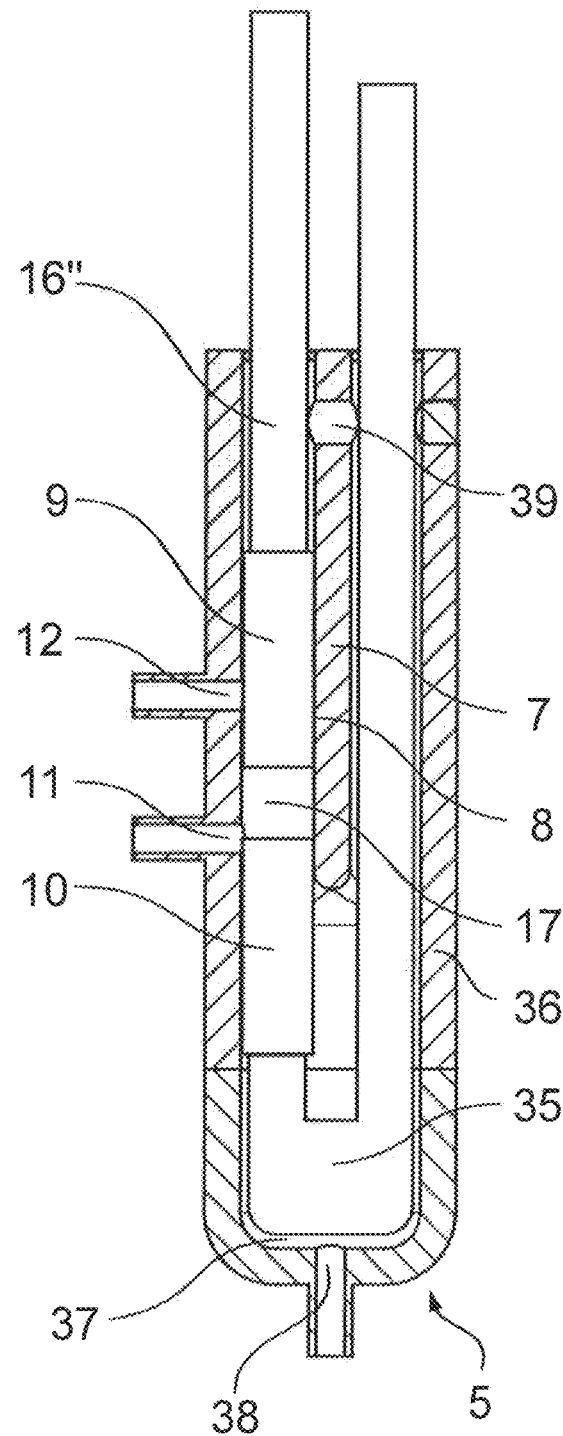
Figure 14C:
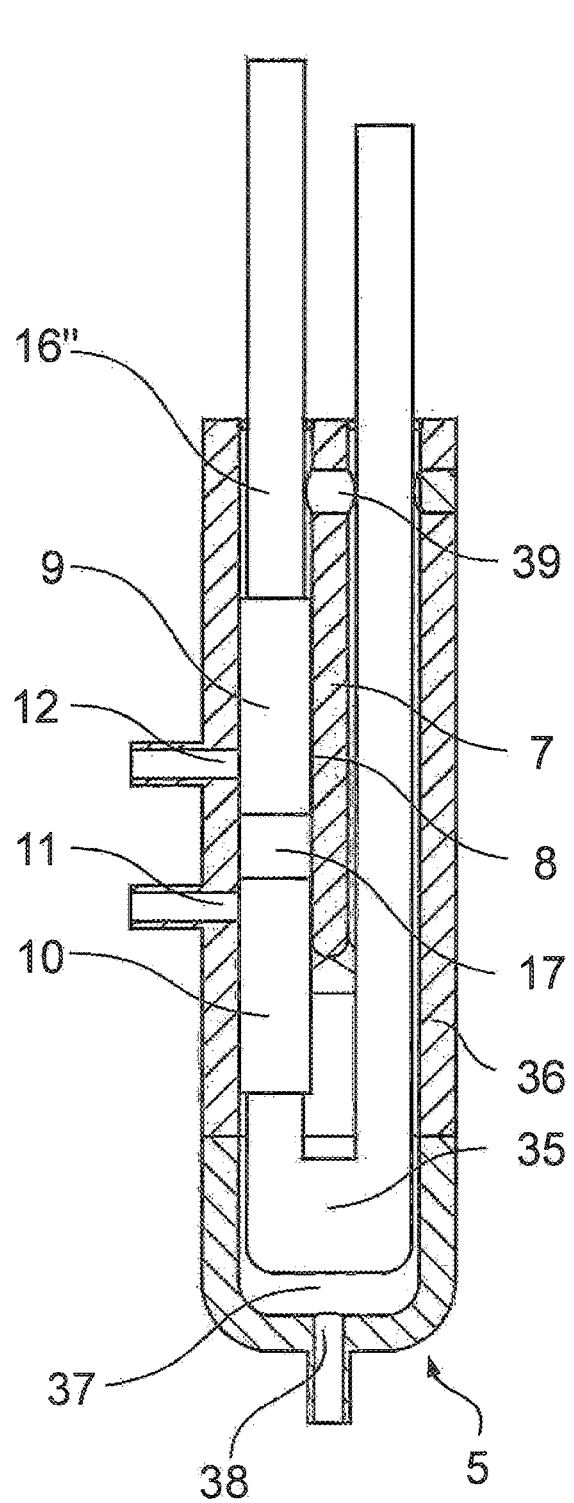
Figure 14D:
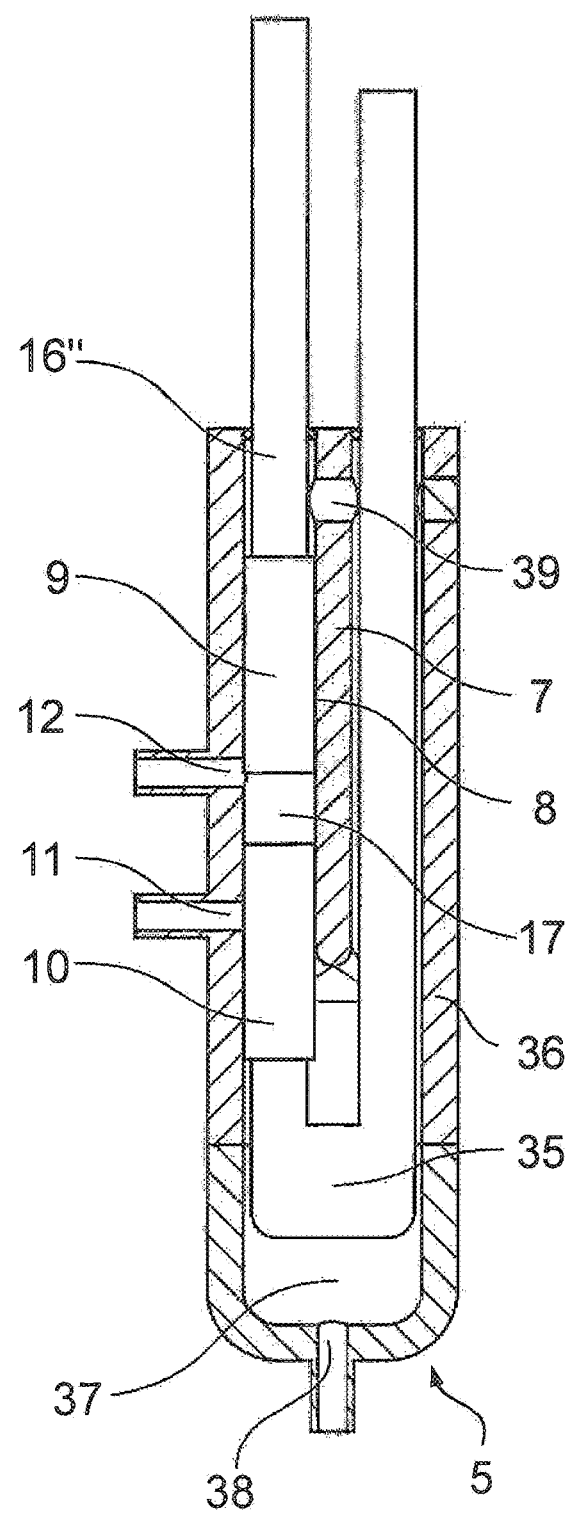
Figure 14E:
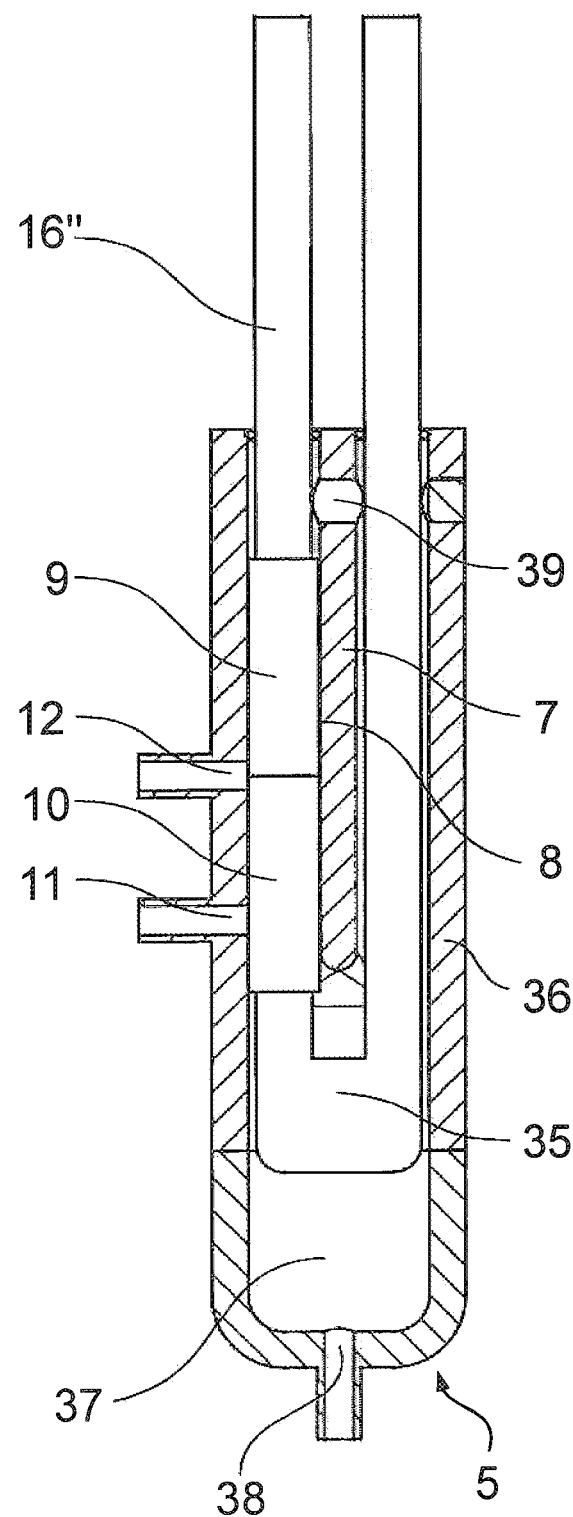

Further advantages and individual features of the invention may be derived from the following description of a plurality of exemplary embodiments and from the drawings in which, in a schematic manner:

FIG. 1: Shows a perspective illustration of a dosing apparatus according to the invention;

FIGS. 2a-2f: Show a series of longitudinal sections through a conveying device of a dosing apparatus according to the invention, for visualizing a pumping procedure;

FIG. 3: Shows a longitudinal section through a conveying device of a dosing apparatus according to the invention, having a pressure sensor;

FIGS. 4a-4d: Show a series of longitudinal sections through a conveying device of a dosing apparatus according to the invention, for visualizing a filling procedure;

FIGS. 5a-5d: Show a longitudinal section through a conveying device of an alternative exemplary embodiment of a dosing apparatus according to the invention, for visualizing a filling procedure;

FIG. 6: Shows a longitudinal section through a conveying device of a dosing apparatus according to the invention, having two independent conveying drives;

FIG. 7: Shows a longitudinal section through a conveying device of an alternative exemplary embodiment of a dosing apparatus according to the invention, having two independent conveying drives;

FIG. 8: Shows a longitudinal section through a conveying device of a dosing apparatus according to the invention, having three intake openings;

FIGS. 8a-8i: Show a series of part-enlargements through longitudinal sections of a conveying device according to FIG. 8, for visualizing a pumping procedure;

FIG. 9: Shows a longitudinal section through a conveying device of a dosing apparatus according to the invention, having an additional analysis opening;

FIGS. 9a-9j: Show a series of part-enlargements of longitudinal sections through a conveying device according to FIG. 9, for visualizing an analysis and pumping procedure;

FIGS. 10a-10e: Show a series of longitudinal sections through a conveying device of a dosing apparatus according to the invention, having a common drive for both pistons;

FIGS. 11a-11e: Show a series of longitudinal sections through a conveying device of an alternative exemplary embodiment of a dosing apparatus according to the invention, having a common drive for both pistons;

FIG. 12a: Shows a spatial illustration of a longitudinal section according to FIG. 11c;

FIG. 12b: Shows the bellows 34 marked by a circle in FIG. 12a, but in a non-sectional form;

FIGS. 13a-13d: Show a series of longitudinal sections through a conveying device of an alternative exemplary embodiment of a dosing apparatus according to the invention, having two independent piston drives which are configured as cam gears;

FIGS. 14a-14e: Show a series of longitudinal sections through a conveying device of an alternative exemplary embodiment of a dosing apparatus according to the invention, for installation in a filling station for liquid pharmaceuticals.

FIG. 1 shows a perspective illustration of a dosing apparatus 1 according to the invention. Said dosing apparatus additionally comprises a collapsible container 2, the fluid to be dispensed being contained in the interior 3 thereof. The container 2 is connected to the conveying device 5 via a connection duct 24 in the closure piece 23. The conveying device 5 comprises a cylinder 7 in which a first piston 9 and a second piston 10 are displaceably mounted. An intake opening 11 for suctioning the fluid from the container 2 is attached to the cylinder 7. In order for the fluid to be dispensed from the dosing apparatus 1, an outlet opening 12 which is fluidically connected with the dispensing opening 6 is moreover attached to the cylinder 7. In the exemplary embodiment shown, additionally a pressure sensor 13 as well as a filling opening 14 which is closed off by a stopper 22 are attached to the cylinder 7. The first piston 9 and the second piston 10 in the exemplary embodiment shown are driven by a common conveying drive 4 which here is configured as a spindle drive.

Figure 2A:
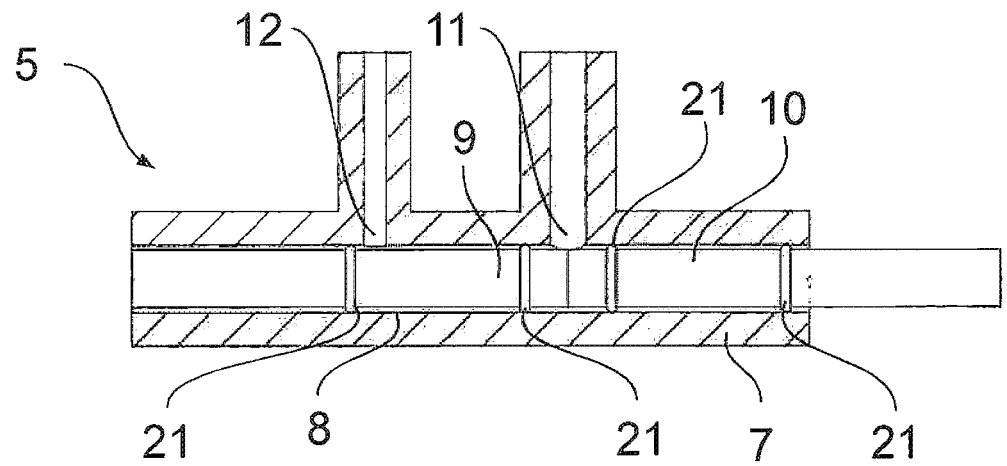
Figure 2B:
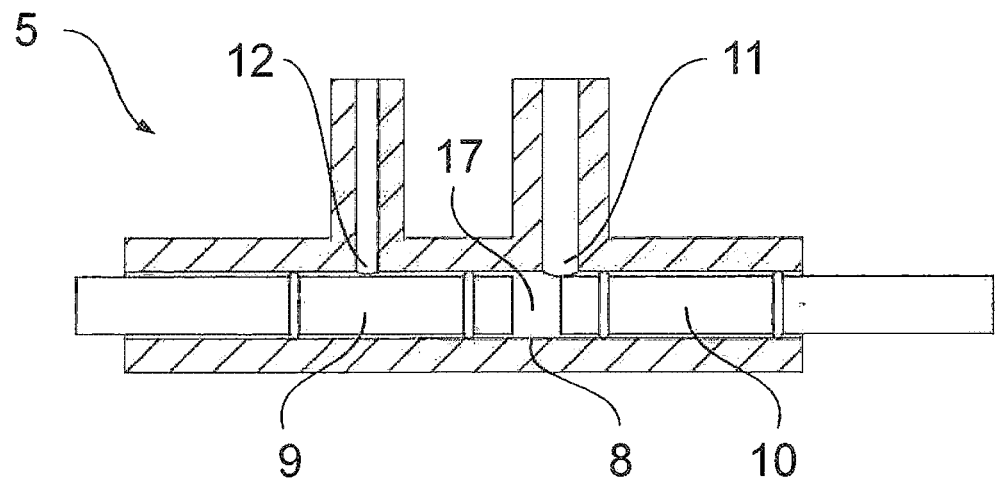
Figure 2C:
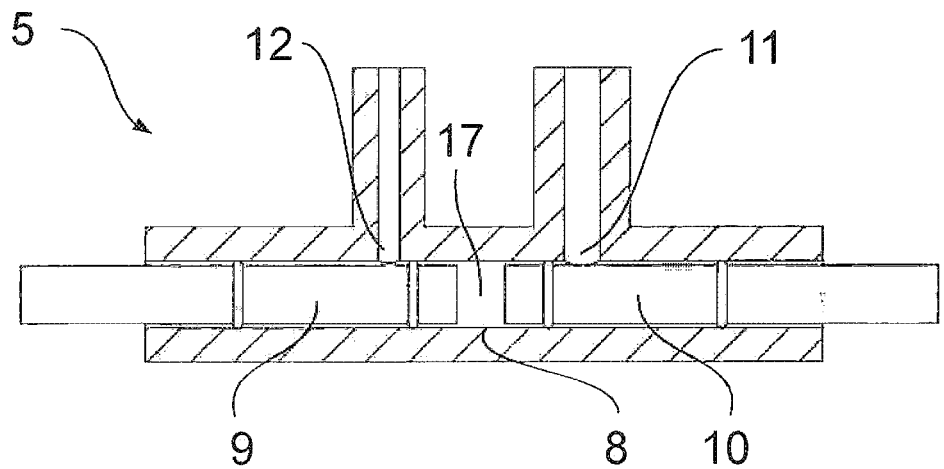
Figure 2D:
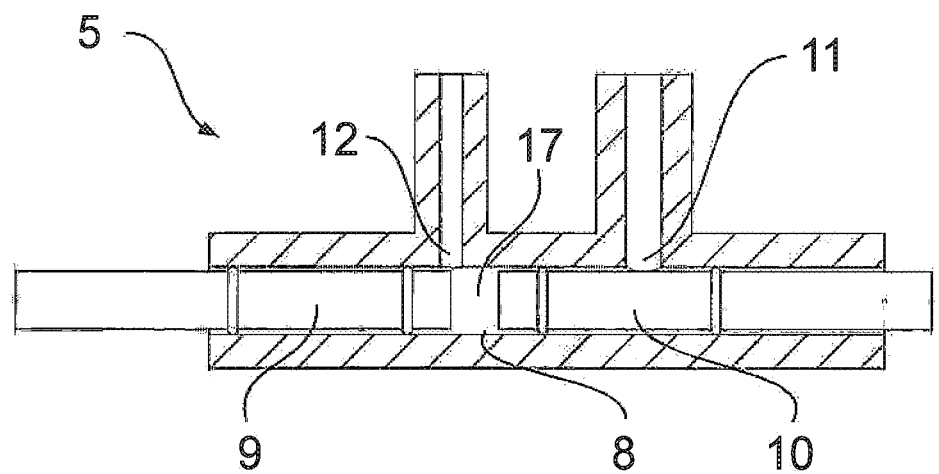
Figure 2E:
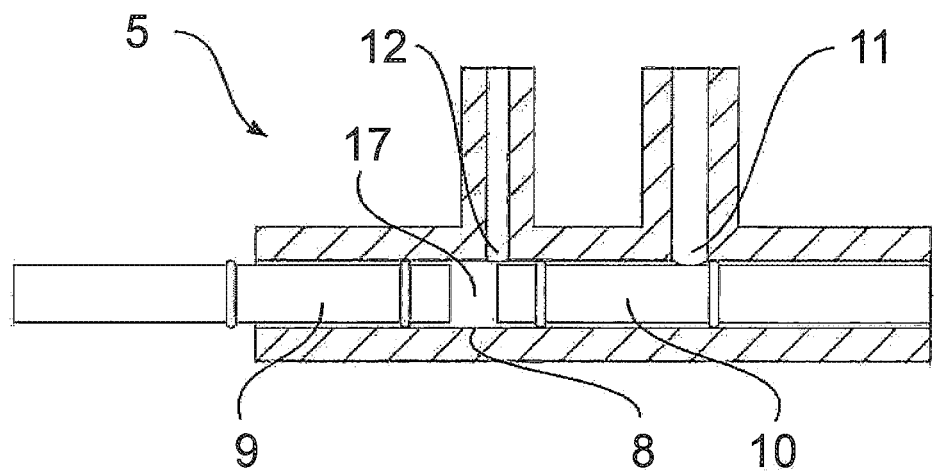
Figure 2F:
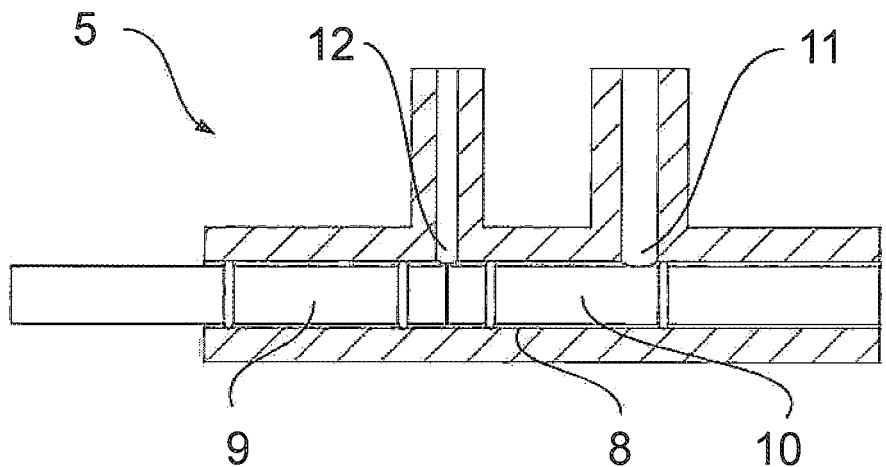

The operating principle of the conveying device 5 of a dosing apparatus 1 according to FIG. 1 is illustrated in FIGS. 2a-f. FIG. 2a shows a longitudinal section through the conveying device 5 in the initial state thereof. The two pistons 9 and 10 are mounted so as to be displaceable in the cylinder 7. In order for a fluid-tight contact between the pistons 9 and 10 and the inner cylinder wall 8 to be established, a plurality of annular seals 21 are attached to the pistons 9 and 10. Moreover, an intake opening 11 and an outlet opening 12 are present on the cylinder 7 of the conveying device 5. In the initial position of the conveying device 5, the two pistons 9 and 10, having end-side contact, are positioned so as to be level with the intake opening 11. FIG. 2b shows the conveying device 5 after suctioning of fluid has been performed. It can be seen that the first piston 9 has been displaced in the direction of the outlet opening 12, on account of which a volume 17 which is delimited internally and by the inner cylinder wall 8 has been formed between the end sides of the two pistons 9 and 10. In FIG. 2c the two pistons 9 and 10 are displaced in the direction of the outlet opening 12, so as to be mutually equidistant. In FIG. 2d, the first piston 9 in the longitudinal direction of the cylinder 7 is now level with the outlet opening 12. In order for the liquid to be ejected, the second piston 10, proceeding from this position, may displaced further in the direction of the first piston 9 up to the point at which the two pistons 9 and 10 have end-side contact, as is shown in FIG. 2f. However, the two pistons 9 and 10, proceeding from a position according to FIG. 2d, may also be further displaced in an equidistant manner up to the point where the second piston 10 is level with the outlet opening 12, corresponding to FIG. 2e. Proceeding from here, an alternative ejection principle, in which the first piston 9 is displaced in the direction of the second piston 10, is implementable.

FIG. 3 shows an alternative exemplary embodiment of a conveying device 5 of a dosing apparatus 1 according to the invention, in which additionally a pressure sensor 13 is attached to the cylinder 7, so as to be level with the outlet opening 12.

Figure 4A:
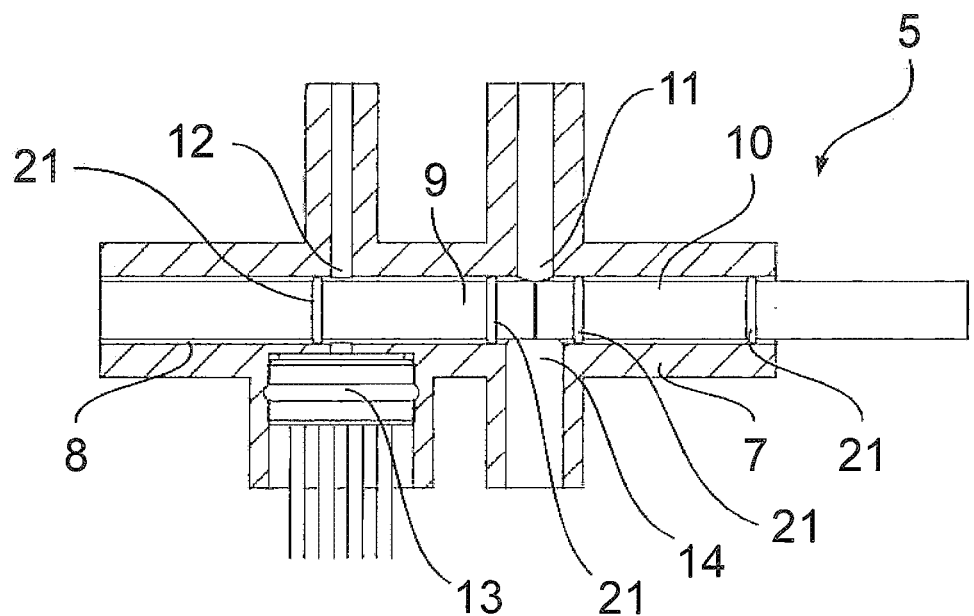
Figure 4B:
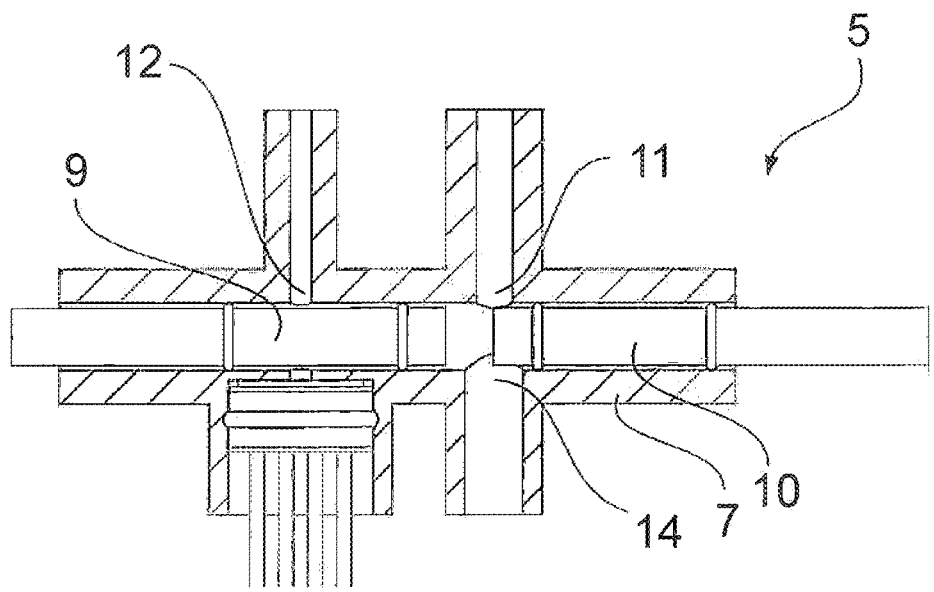
Figure 4C:
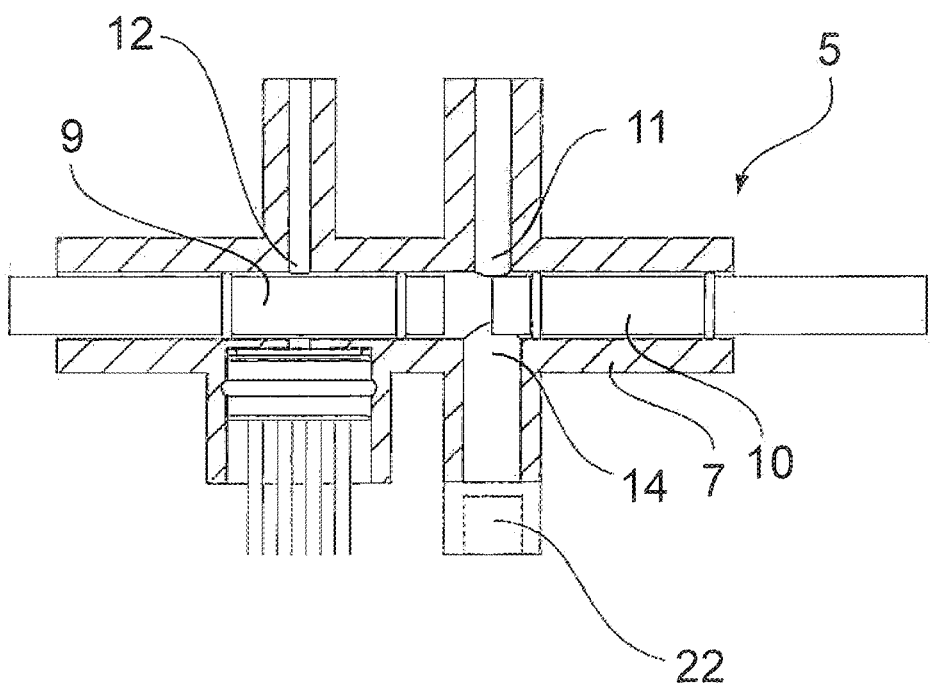
Figure 4D:
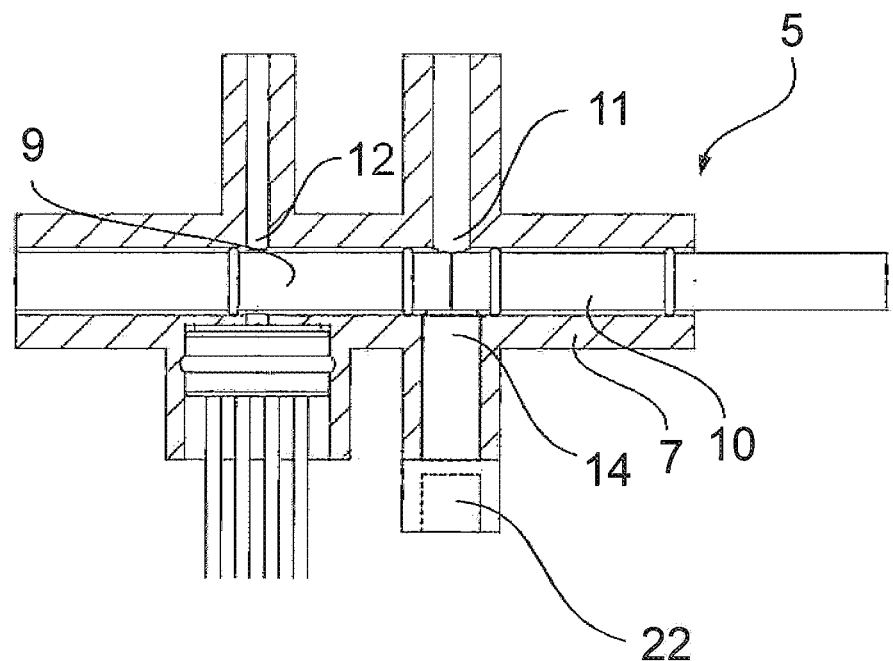

A sequence of longitudinal sections through the conveying device 5 of a further exemplary embodiment of a dosing apparatus 1 according to the invention is shown in FIGS. 4a-d. An additional filling opening 14 is attached to the cylinder 7 in the case of said conveying device. FIG. 4a shows the conveying device 5 in the initial position thereof, prior to filling the container 2. The two pistons 9 and 10, having end-side contact, in the longitudinal direction of the cylinder 7 are positioned so as to be level with the intake opening 11 and the filling opening 14. As can be seen in FIG. 4b, fluid communication between the filling opening 14 and the intake opening 11 is established by displacing the first piston 9 in the direction of the outlet opening 12. The interior 3 of the container 2 may be filled with fluid on account of this fluid communication. After the filling procedure has been performed, the filling opening 14 is closed according to FIG. 4c, using a stopper 22. In FIG. 4d, the conveying device 5 having a filled container 2 is again shown in the initial position of the former.

Figure 5A:
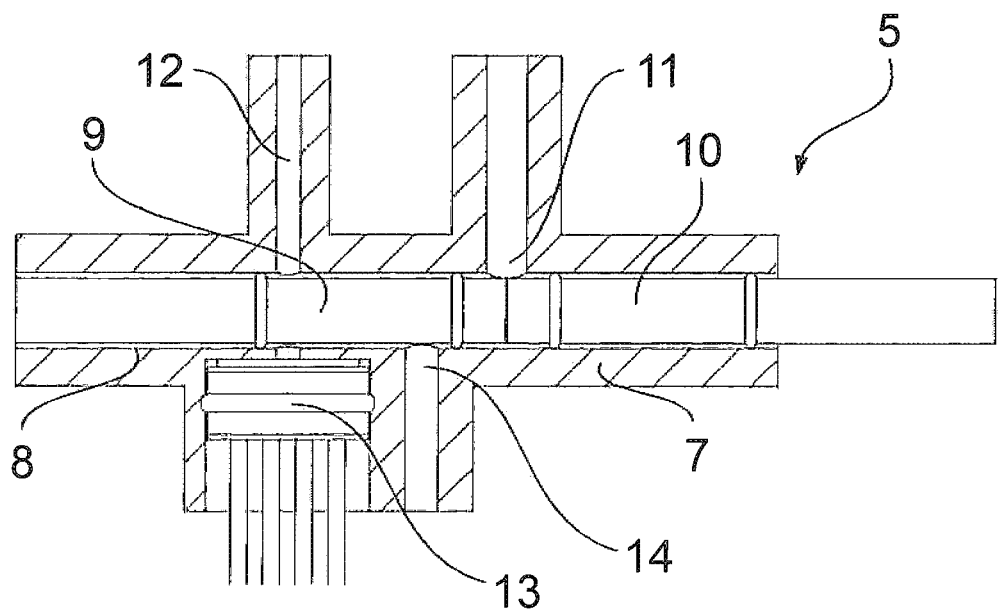
Figure 5B:
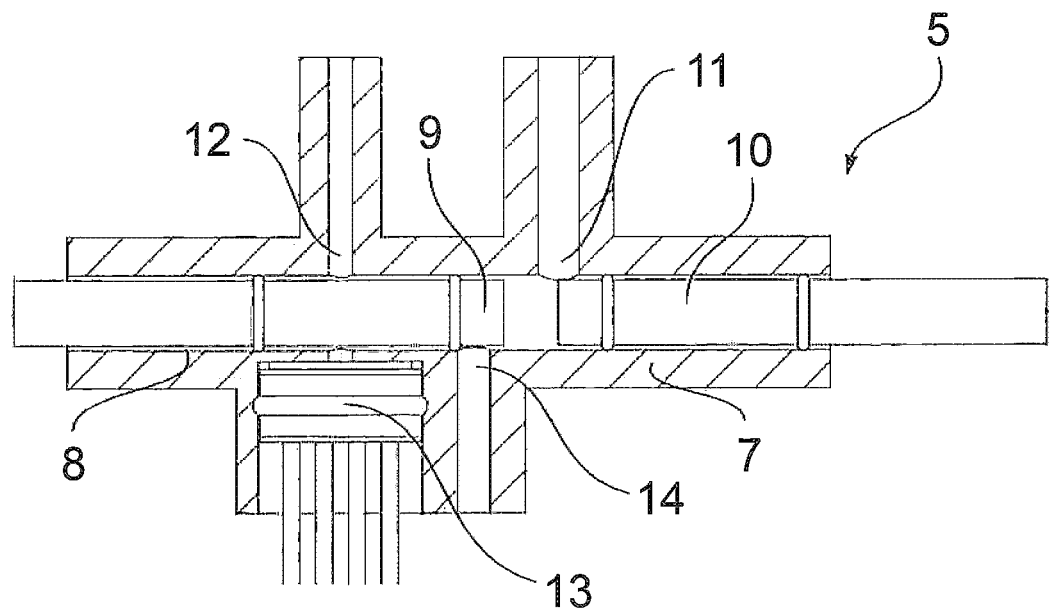
Figure 5C:
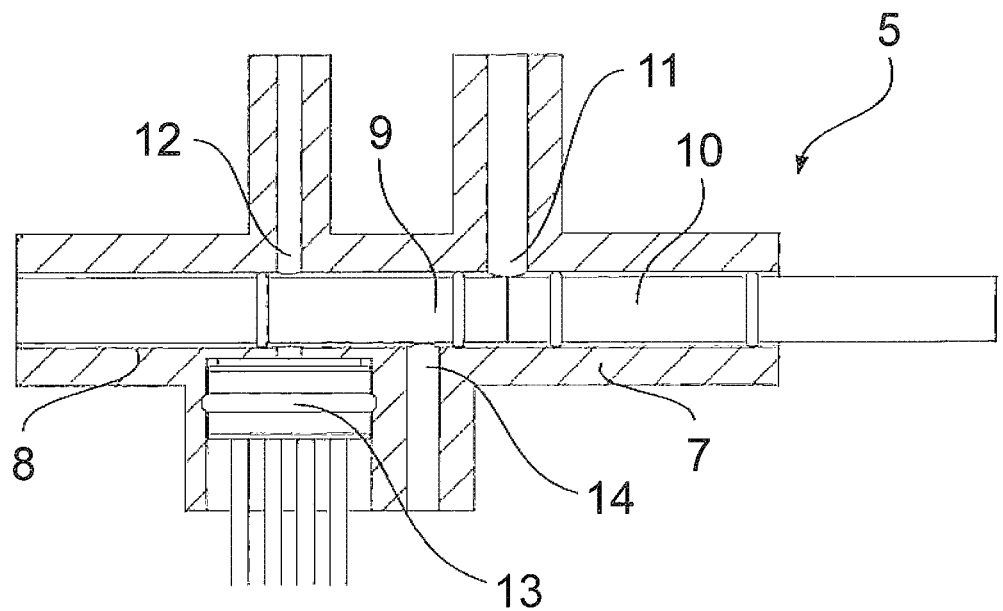
Figure 5D:
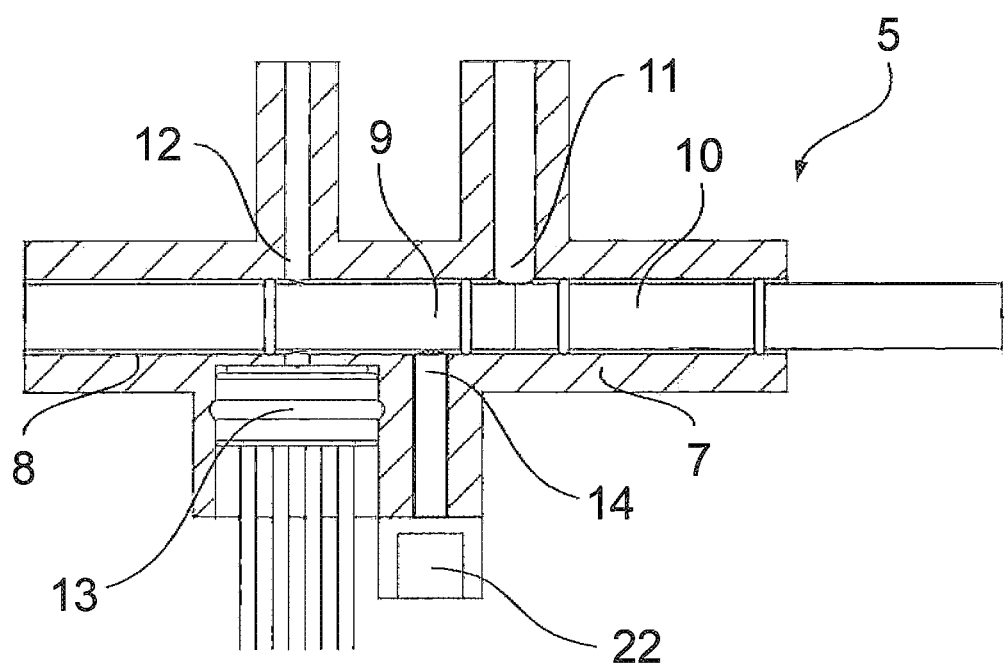

FIGS. 5a-d highlight the filling procedure of an alternative exemplary embodiment of a dosing apparatus 1 according to the invention. A longitudinal section through a corresponding conveying device 5 in which the filling opening 14 and the intake opening 11 are disposed on the cylinder 7 so as to be offset in the longitudinal direction is shown in FIG. 5a. In order for the dosing apparatus 1 to be filled, the first piston 9 is displaced in the direction of the outlet opening 12 (FIG. 5b), so as to establish fluid communication between the filling opening 14 and the intake opening 11. As is illustrated in FIG. 5c, said fluid communication may again be interrupted after filling of the container 2 has been performed, by again displacing the piston 9 in the direction of the second piston 10. The filling opening 14 is closed off using a stopper 22 as the last step of the filling procedure (FIG. 5d).

FIG. 6 shows a part-section through a dosing apparatus 1 according to the invention, in which the conveying device 5 is driven by two independent conveying drives 4 and 4'. The two conveying drives 4 and 4' here are of identical construction and comprise in each case one motor 25 having a transmission 26. The rotation movement generated by the motor 25 is transmitted to a spindle housing 28 which is rotatably mounted by way of the bearings 29. The spindle housing 28 has a bore having a thread 30 into which the spindle 27 engages. On account thereof, a rotation movement which has been generated by the motor and the transmission 26 may be converted into a longitudinal movement of the piston 9 or 10. In said exemplary embodiment, a filling opening 14 is attached to the conveying device 5, so as in the longitudinal direction to be level with the intake opening 11, and is closed off by way of a stopper 22.

FIG. 7 shows an alternative exemplary embodiment of a dosing apparatus 1 according to the invention, having the conveying drive 4 and 4' according to FIG. 6. However, the filling opening 14 here is disposed on the cylinder 7 of the conveying device 5, so as to be offset in the longitudinal direction in relation to the intake opening 11.

Figure 8B:
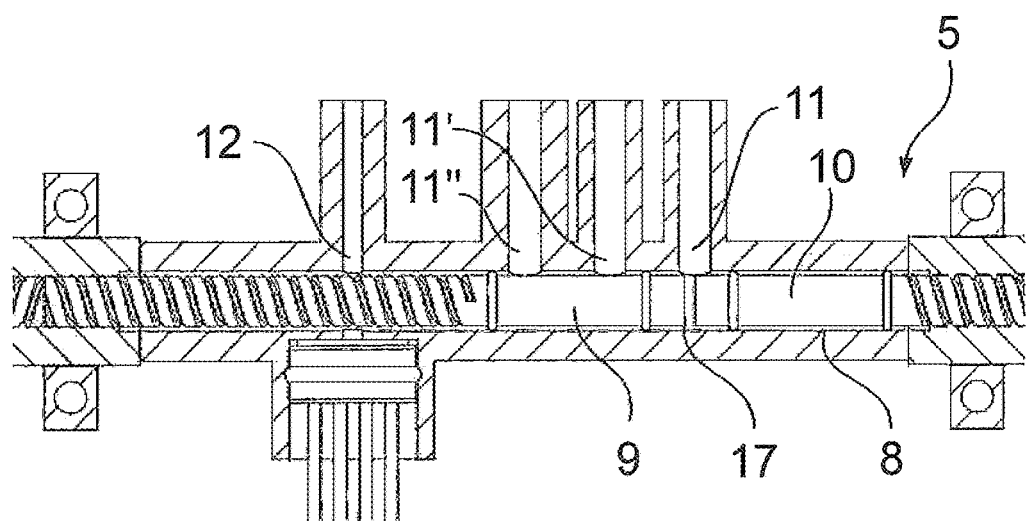
Figure 8C:
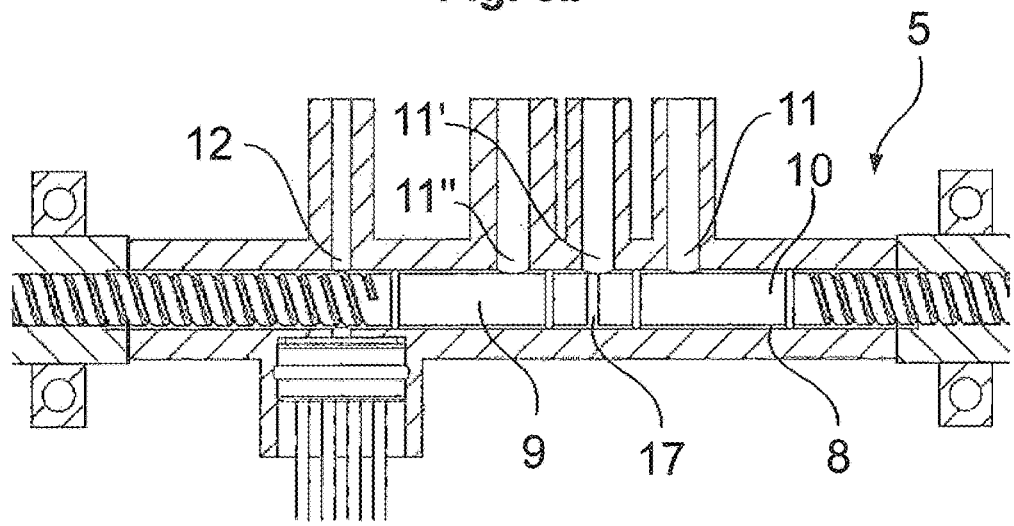
Figure 8D:
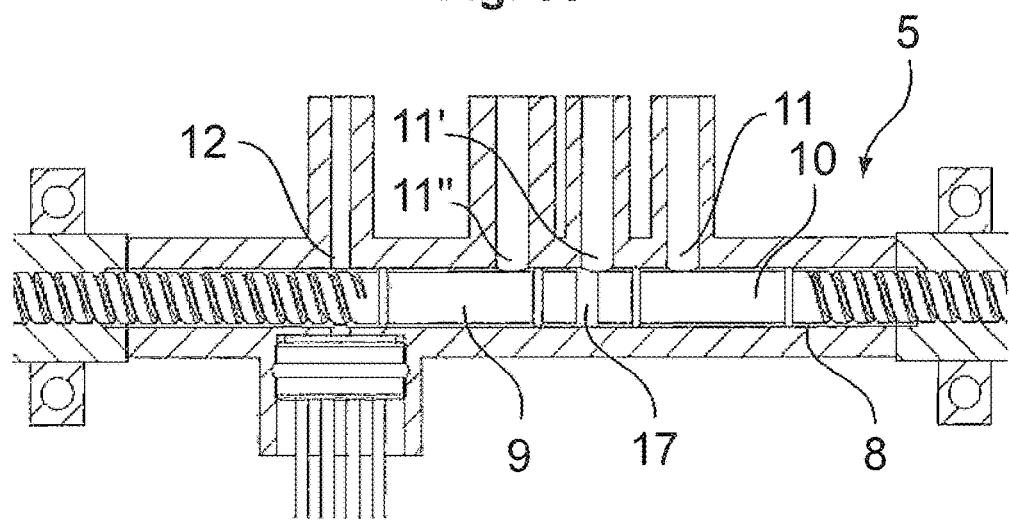
Figure 8E:
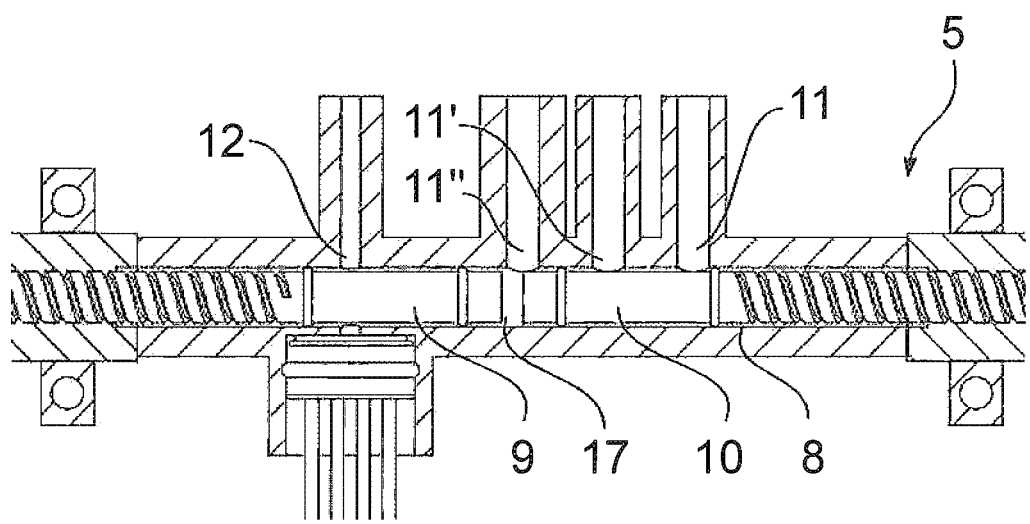
Figure 8F:
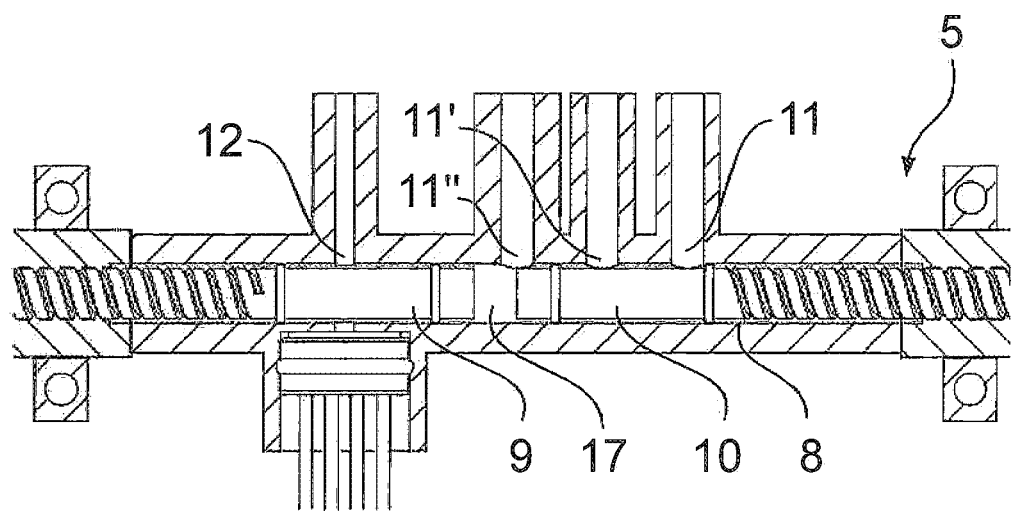
Figure 8G:
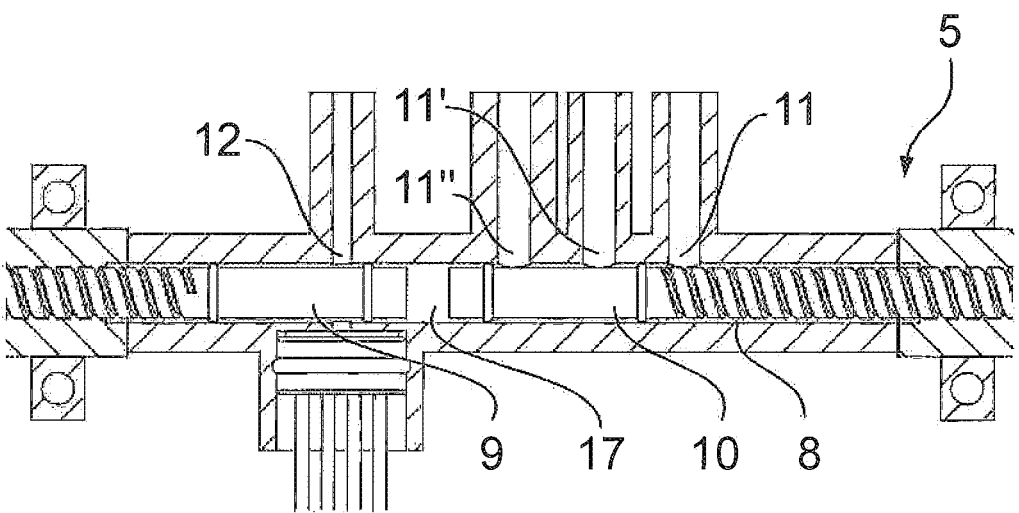
Figure 8H:
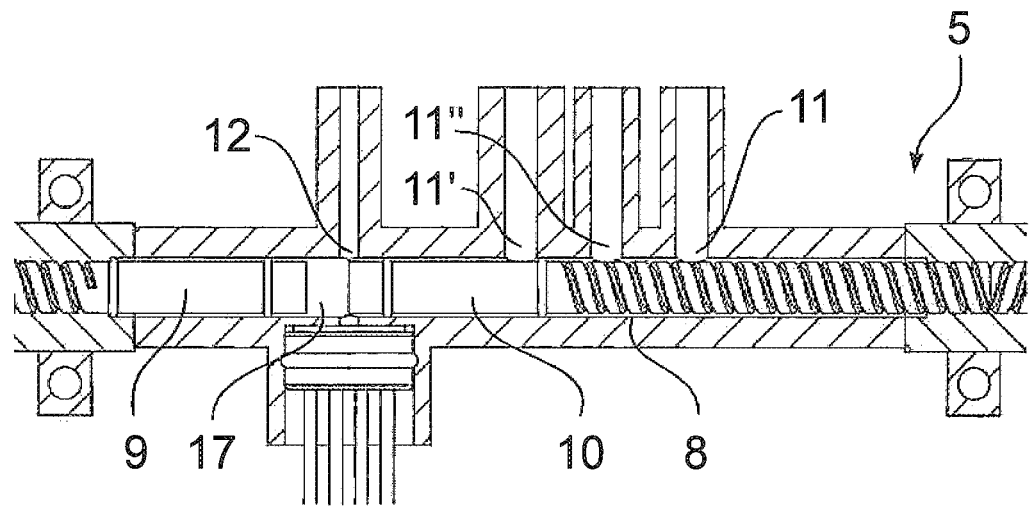
Figure 8I:
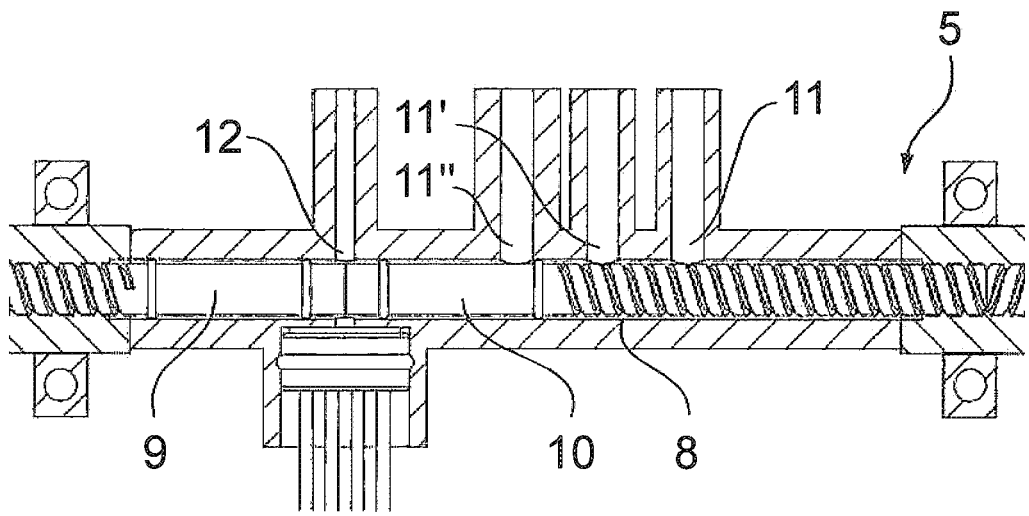
Figure 9B:
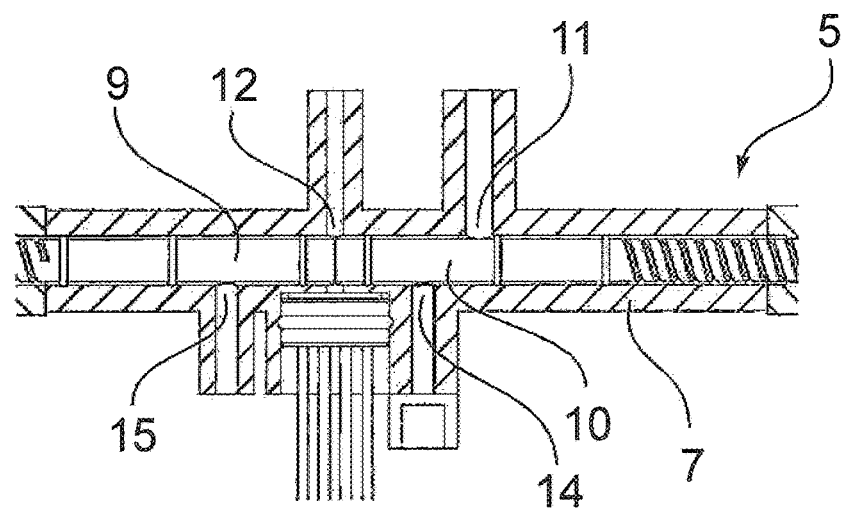
Figure 9C:
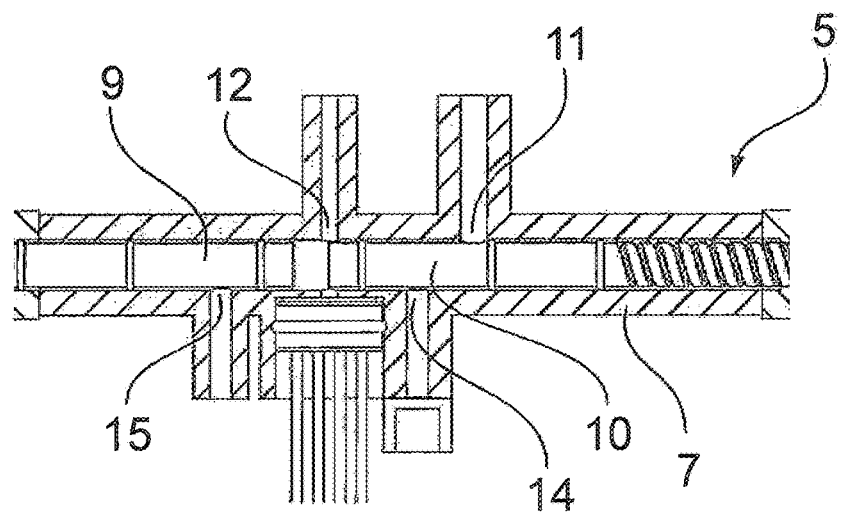
Figure 9D:
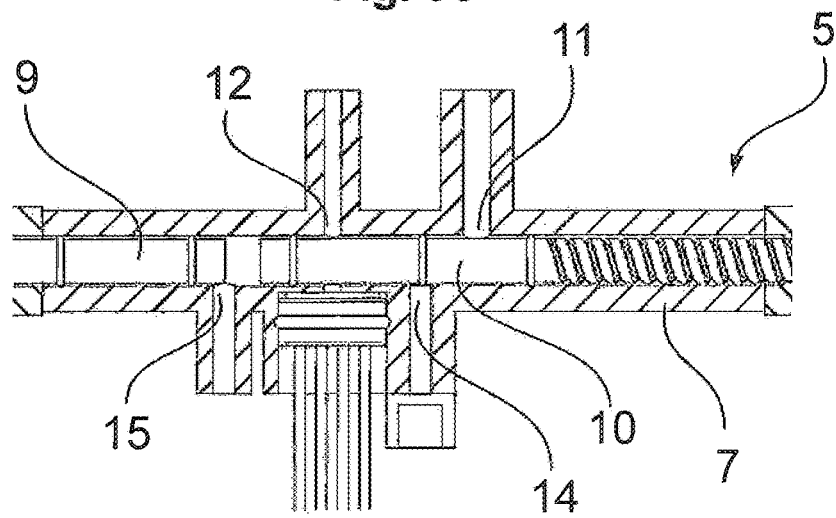
Figure 9E:
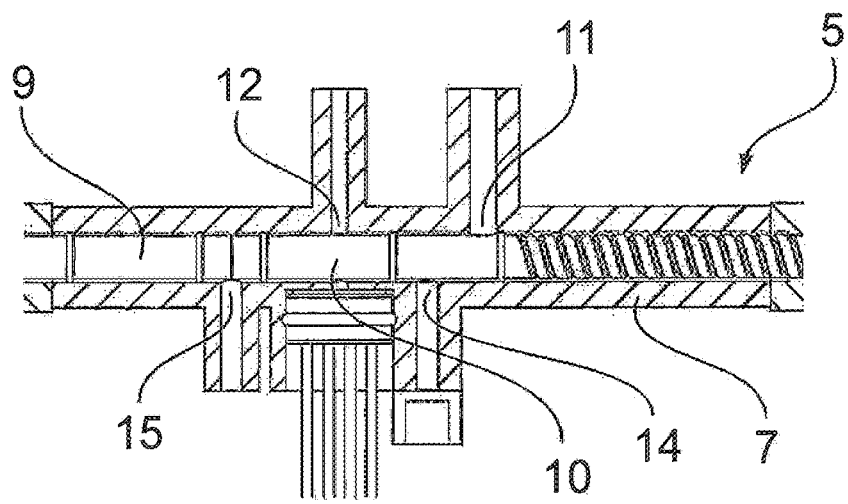
Figure 9F:
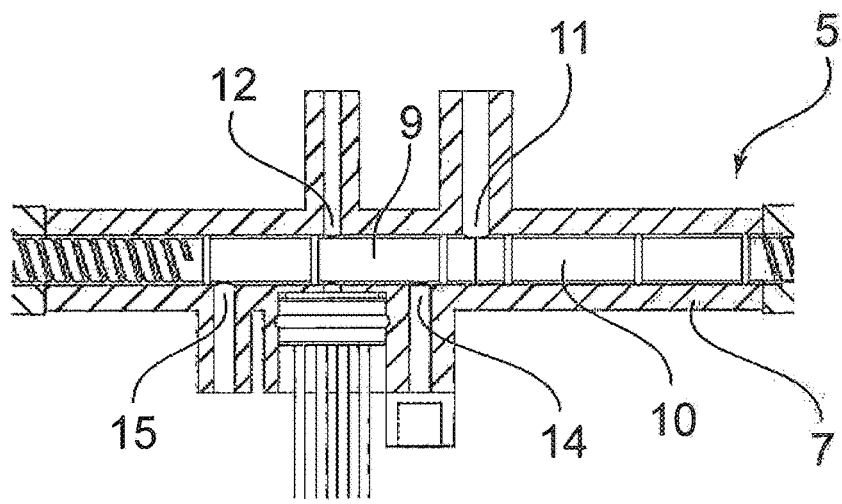
Figure 9G:
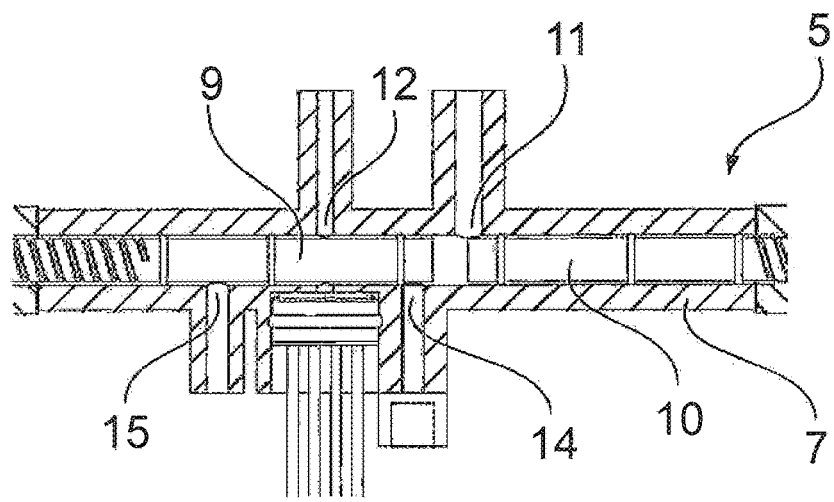
Figure 9H:
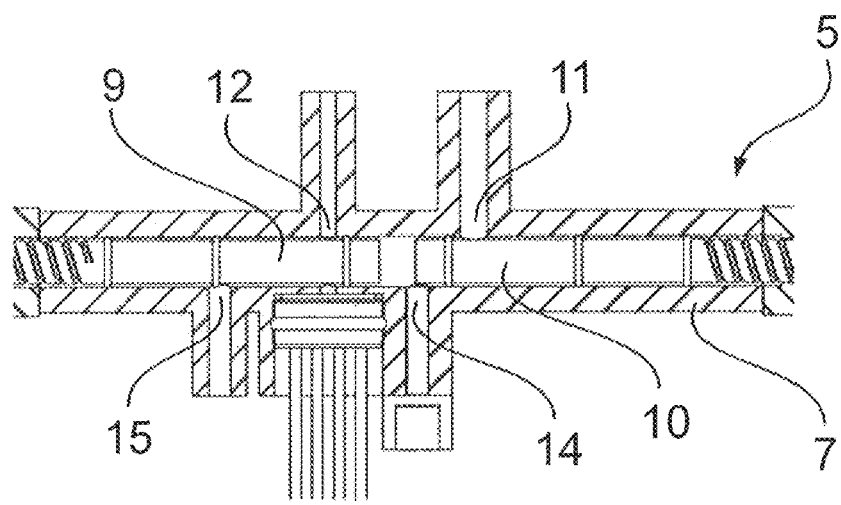
Figure 9I:
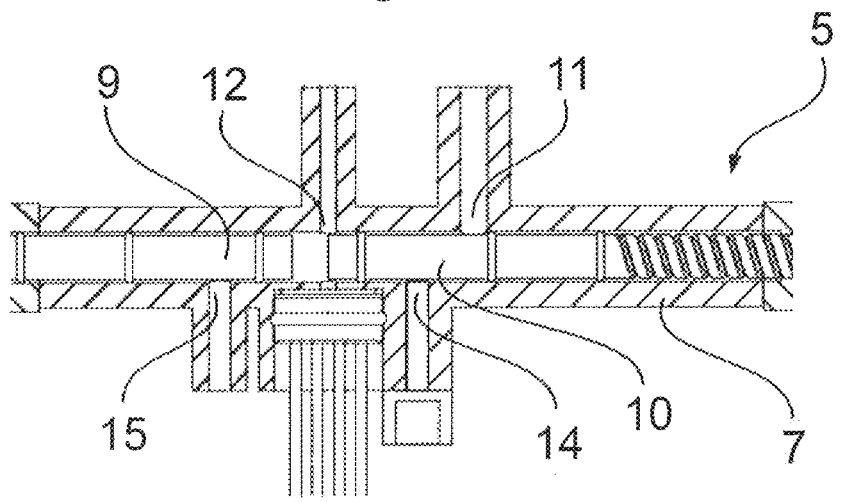
Figure 9J:
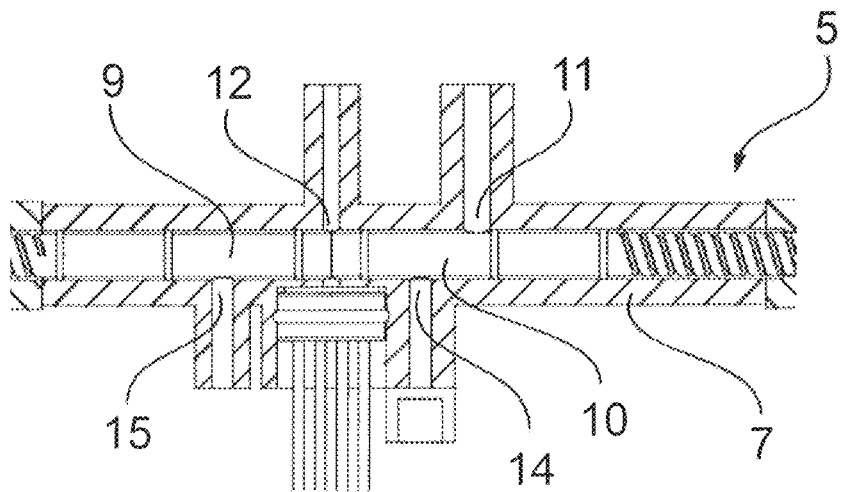

FIG. 8 shows a further exemplary embodiment of a dosing apparatus 1 according to the invention, having a conveying device 5 which has three independent intake openings 11, 11', and 11". FIGS. 8a-i represent a series of longitudinal sections of said conveying device 5, corresponding to a part-enlargement of FIG. 8. In FIG. 8a the conveying device 5 is shown in the initial position thereof, wherein the first piston 9 and the second piston 10 are in end-side contact, so as to be level with the first intake opening 11. In FIG. 8b the first piston 9 is displaced in the direction of the outlet opening 12, on account of which a volume 17 for suctioning fluid is formed between the end sides of the first piston 9 and of the second piston 10 and the inner cylinder wall 8. In FIG. 8c the two pistons 9 and 10 in the longitudinal cylinder direction are displaced in an equidistant manner, so as to be level with the second intake opening 11'. By again moving the first piston 9 in the direction of the outlet opening 12, further fluid may be suctioned through the intake opening 11' (FIG. 8d). In FIG. 8e, the two pistons 9 and 10 are again offset in an equidistant manner in the direction of the dispensing opening 12, so as to be level with the third intake opening 11". Here too, fluid may be suctioned through the intake opening 11" by displacing the first piston 9 in the direction of the outlet opening 12 (FIG. 8f). FIG. 8g shows equidistant displacement of the first piston 9 and of the second piston 10 in relation to the dispensing opening 12. FIG. 8h illustrates the conveying device 5 in the ready state for dispensing, with the second piston 10 being level with the outlet opening 12. After the fluid has been dispensed by displacing the first piston 9 in the direction of the second piston 10, there is again end-side contact between the two pistons 9 and 10, as is shown in FIG. 8i.

FIG. 9 shows a longitudinal section through a further exemplary embodiment of a dosing apparatus 1 according to the invention, having an additional analysis opening 15 on the cylinder 7 of the conveying device 5. The corresponding conveying device 5 is shown in part-enlargement in FIG. 9a. The two pistons 9 and 10 are located in the initial position, the end sides thereof in the longitudinal direction of the cylinder 7 being level with the intake opening 11. In a first step, the two pistons 9 and 10 are displaced so as to be level with the outlet opening 12, as is highlighted in FIG. 9b. Thereafter, fluid, for example a patient's blood, is received in the dosing apparatus 1 through the outlet opening 12 by moving the first piston 9 in the direction of the analysis opening 15 (FIG. 9c). The received fluid by equidistant displacement of the pistons 9 and 10 is thereafter moved to the analysis opening 15 (FIG. 9d). The fluid is dispensed through the analysis opening 15 to an analysis device by moving the second piston 10 in the direction of the first piston 9. Once dispensing has been performed, the conveying device 5 having end-side contact between the first piston 9 and the second piston 10 according to FIG. 9e is established. Accordingly, the pistons are thereafter collectively offset to the initial position according to 9f. As is shown in FIGS. 9g-j, thereafter a dosage of fluid which has been determined by the analysis device may be taken into the conveying device 5 and dispensed to a patient.

Figure 10A:
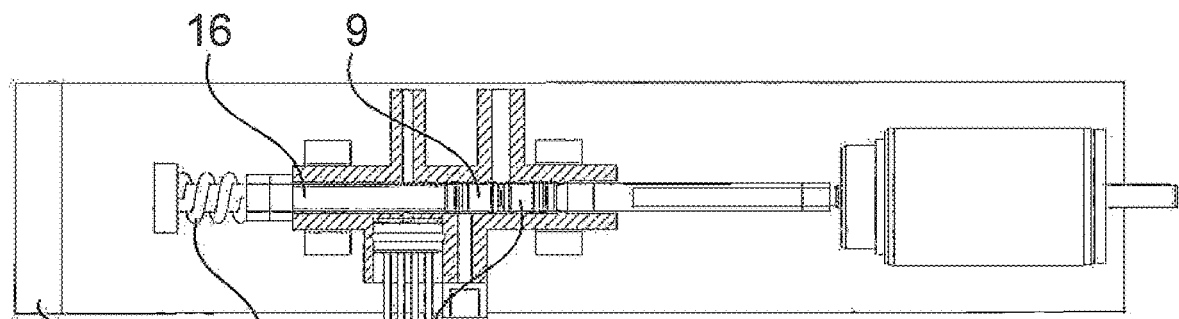
Figure 10B:
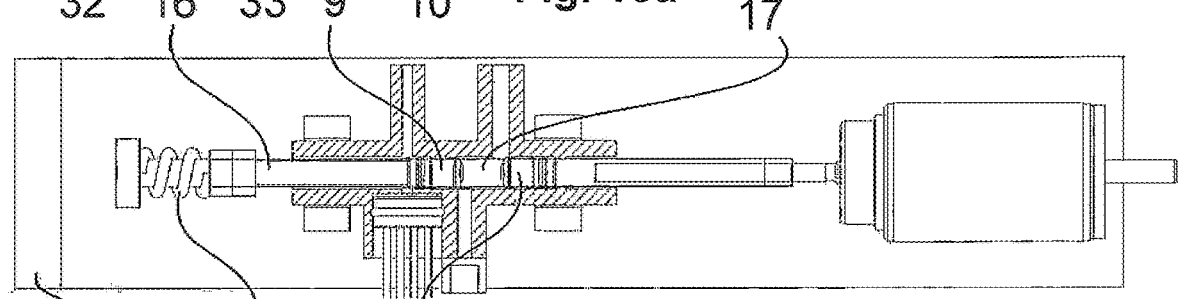
Figure 10C:
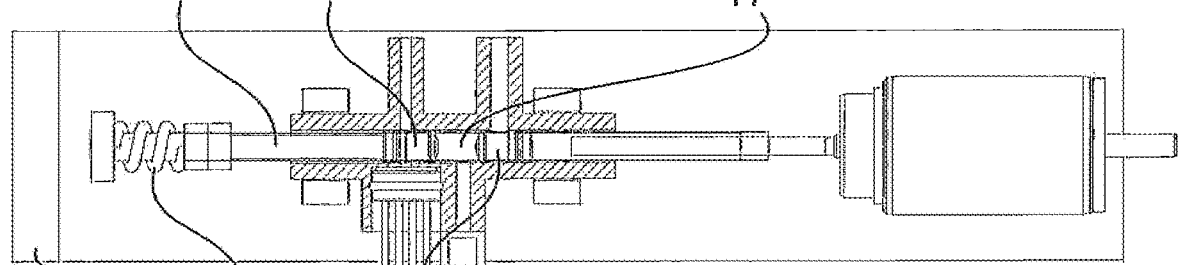
Figure 10D:
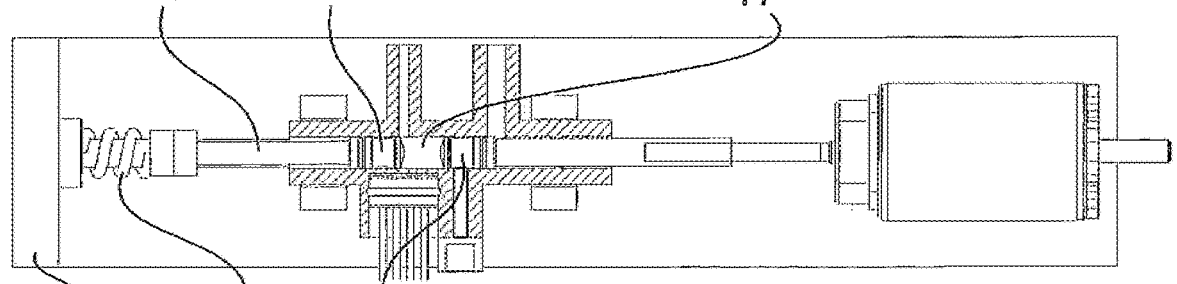
Figure 10E:
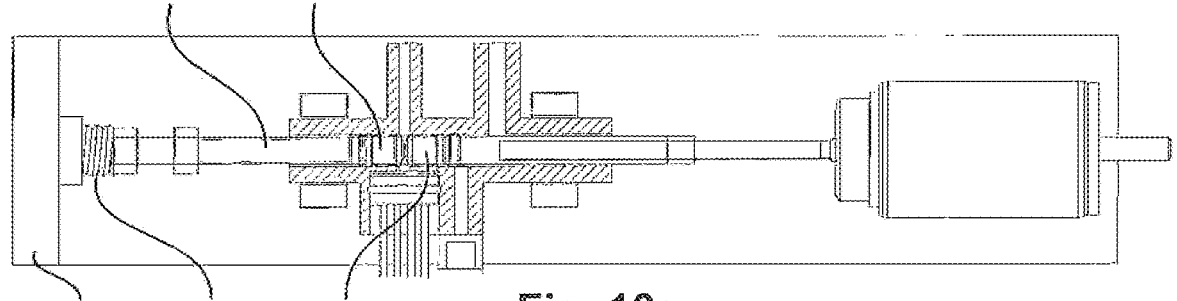
Figure 11E:
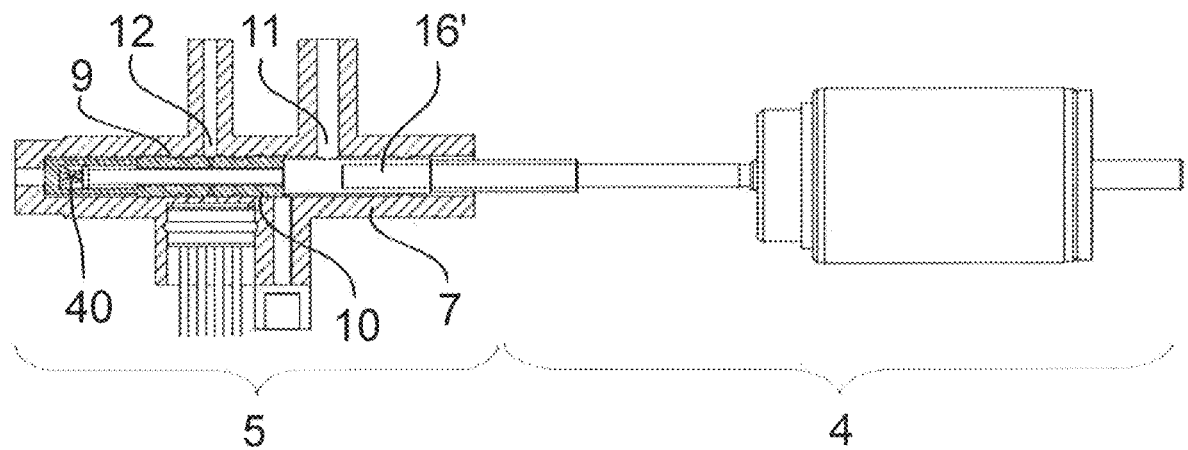

FIGS. 10a-e show an exemplary embodiment of a dosing apparatus 1 according to the invention, in which the two pistons 9 and 10 of the conveying device 5 are driven by a common conveying drive 4. The first piston 9 here is indirectly coupled via a compression spring 33 to the conveying drive 4, while the second piston 10 is connected in a floating manner to the conveying drive 4. As can be seen in FIG. 10b, actuation of the conveying drive, proceeding from the initial position in FIG. 10a, first leads to sole displacement of the first piston 9 in the direction of the outlet opening 12. Once the desired fluid volume 17 between the two pistons 9 and 10 has been reached, the second piston 10 is displaced in an equidistant manner to the first piston 9 in the direction of the dispensing opening 12, as is shown in FIG. 10c. In FIG. 10d the first piston 9 in the longitudinal direction of the cylinder 7 has now reached a position which is level with the dispensing opening 12. It can be seen that the piston rod 16 of the first piston at this point also contacts the stop 32. Further actuation of the conveying drive 4 leads to the spring 33 being compressed, as is shown in FIG. 10e, on account of which the second piston 10 is further displaced in the direction of the dispensing opening 12, again leading to dispensation of the fluid volume having been taken in.

FIGS. 11a-e show a further exemplary embodiment of a dosing apparatus 1 according to the invention, in which the conveying device 5 is driven by only one conveying drive 4. The first piston 9 here is operatively connected in an indirect manner via the spring element 40 which is disposed therein with the conveying drive 4. The second piston 10 by way of the piston rod 16' may be pushed in the direction of the outlet opening 12, and by way of the first piston 9 in the direction of the intake opening 11. The first piston 9 and the second piston 10 are configured so as to be integral and are interconnected by way of a bellows 34. In this way, the pistons 9 and 10 and the bellows 34 may be implemented from a single part, for example from silicone, TPE, or bromobutyl rubber, for example.

FIG. 12a shows a spatial illustration of a longitudinal section according to FIG. 11c. It can be seen that the first piston 9 and the second piston 10 are displaced in an equidistant manner in the direction of the outlet opening 12. Here, the first piston 9 is moved by way of the spring element 40, and the second piston 10 is pushed by the piston rod 16'. FIG. 12b shows the bellows 34 which is marked by a circle in FIG. 12a, but not as part-section but in a spatial illustration.

FIGS. 13a-d show a further dosing apparatus 1 according to the invention, in which the pistons 9 and 10 of the conveying device 5 are driven by two independent conveying drives 4 and 4'. However, in this case, these are two cam gears 18 and 18'. Said cam gears 18 and 18' comprise in each case one control disc 19 having a guide groove 31 by way of which a plunger 20 is articulated thereon.

FIGS. 14a-e show the conveying device 5 of a further alternative exemplary embodiment of a dosing apparatus 1 according to the invention, for installation in a filling station for liquid pharmaceutical formulae. The conveying device 5 in this case has a cylinder 7 which is integrally embodied as a U-shaped housing 36. While the first piston 9 transitions into a typical straight piston rod 16", the second piston 10 is connected to a U-shaped piston rod 35 which has a bend of 180°. The conveying device 5 is not only without a valve, but is also conceived so as to have no seals or piston rings on the pistons. The housing 36 has a space 37 for the bend in the piston rod 35, and ducts 38 and 39 for flushing the conveying device 5.

The invention claimed is:

1. A dosing device for dispensing a fluid under aseptic conditions, where the dosing device comprises:
   a dispensing module comprising:
      a container having an interior that is collapsible and non-venting,
      a conveying device which is driven by a conveying drive to convey the fluid out of the interior of the container, through an intake opening located on a cylinder of the conveying device, then through an inner wall of the cylinder and through the cylinder to exit an outlet opening positioned on the inner wall a longitudinal distance from the intake opening, where the fluid exiting the outlet opening is conveyed to a dispensing opening,
      a filling opening located on the cylinder and in fluid communication with the inner wall, where the filling opening is located between the intake opening and the outlet opening and offset in a longitudinal direction from the intake opening, and
      a first piston and a second piston slidably positioned within the cylinder and movable in the longitudinal direction between a dispensing position and a filling position; and
   a drive module comprising parts of the conveying drive,
   wherein when the first piston and the second piston are in the dispensing position, end faces of each piston and together with a portion of the cylinder inner wall, delimit a variable fluid volume that has been removed from the container,
   wherein when the first piston and the second piston are in the filing position, end faces of each piston and together with a portion of the cylinder inner wall define a fluid communication path between the filling opening and the intake opening such that fluid will move through the filling opening from a fluid source that is coupled to the filling opening, through the cylinder and into the interior of the container, and,
   wherein the drive module and the dispensing module are configured so as to be mutually connectable and separable by a user of the dosing device.

2. The dosing device according to claim 1, wherein the intake opening and the outlet opening are disposed on the cylinder in a manner offset in the longitudinal direction.

3. The dosing device according to claim 1, wherein the conveying device comprises a second intake opening, which is disposed on the cylinder in a manner offset in the longitudinal direction from the intake opening.

4. The dosing device according to claim 3, wherein the second intake opening is fluidically connectable to an interior of a separate second collapsible container.

5. The dosing device according to claim 3, wherein the first and second intake openings are each fluidically connectable to a separately demarcated interior of the container, wherein the separately demarcated interiors are configured within the container in such a way that at least two fluids are receivable separately from each other from the container.

6. The dosing device according to claim 1, wherein the container additionally comprises a closure piece, wherein the closure piece is disposed fixedly in the container and is fluidically connectable to the conveying device via an attachment channel.

7. The dosing device according to claim 1, wherein the conveying device comprises a first conveying drive and a second conveying drive, wherein the first piston is driven by the first conveying drive, and the second piston is driven by the second conveying drive.

8. The dosing device according to claim 1, wherein the conveying drive is configured as a spindle drive.

9. The dosing device according to claim 1, wherein the dosing device comprises an injection device for continuous subcutaneous dispensing of a fluid to a patient.

10. The dosing device of claim 1 further comprising a valve positioned in the filing opening such that the valve blocks the filling opening with respect to the fluid being conveyed between the intake opening and the outlet opening.

11. The dosing device of claim 1 further comprising a stopper that is positioned in the filling opening when the first piston and second piston are in the dispensing position.

* * * * *